US006627632B2

(12) United States Patent
Parks et al.

(10) Patent No.: US 6,627,632 B2
(45) Date of Patent: Sep. 30, 2003

(54) COMPOSITIONS AND METHODS FOR THE TREATMENT OF ANORECTAL DISORDERS

(75) Inventors: Thomas P. Parks, San Mateo, CA (US); Vivien Mak, Palo Alto, CA (US); Jung-Chung Lee, Sunnyvale, CA (US); Charles Lee, Union City, CA (US)

(73) Assignee: Cellegy Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 09/919,590

(22) Filed: Jul. 30, 2001

(65) Prior Publication Data

US 2002/0072522 A1 Jun. 13, 2002

Related U.S. Application Data

(63) Continuation-in-part of application No. 09/769,621, filed on Jan. 23, 2001, and a continuation-in-part of application No. 09/595,390, filed on Jun. 14, 2000, and a continuation-in-part of application No. 09/460,306, filed on Dec. 13, 1999.
(60) Provisional application No. 60/222,267, filed on Jul. 31, 2000, provisional application No. 60/155,318, filed on Sep. 21, 1999, provisional application No. 60/139,916, filed on Jun. 17, 1999, and provisional application No. 60/112,325, filed on Dec. 14, 1998.

(51) Int. Cl.$^7$ .................. A61K 31/50; A61K 31/495
(52) U.S. Cl. .................. 514/252.19; 514/509
(58) Field of Search ................ 514/742, 740, 514/27, 716, 626, 252.19, 509

(56) References Cited

U.S. PATENT DOCUMENTS

| | | | |
|---|---|---|---|
| 4,562,194 A | * | 12/1985 | Smerbeck et al. ..... 514/263.31 |
| 4,945,084 A | | 7/1990 | Packman |
| 5,196,405 A | | 3/1993 | Packman |
| 5,234,947 A | | 8/1993 | Cherksey |
| 5,437,291 A | | 8/1995 | Pasricha et al. |
| 5,447,947 A | | 9/1995 | Campbell |
| 5,478,814 A | | 12/1995 | Packman |
| 5,492,911 A | | 2/1996 | Stief |
| 5,562,899 A | | 10/1996 | Gerber |
| 5,576,290 A | | 11/1996 | Hadley |
| 5,595,753 A | | 1/1997 | Hechtman |
| 5,693,676 A | | 12/1997 | Gorfine |
| 5,721,215 A | | 2/1998 | Aoki et al. |
| 5,854,291 A | | 12/1998 | Laughlin et al. |
| 5,858,371 A | | 1/1999 | Singh et al. |
| 5,874,437 A | | 2/1999 | Garvey et al. |
| 5,919,776 A | * | 7/1999 | Hagmann et al. ........... 514/159 |
| 5,932,538 A | | 8/1999 | Garvey et al. |
| 5,948,762 A | | 9/1999 | Garfield et al. |
| 5,994,294 A | | 11/1999 | Garvey et al. |
| 6,117,877 A | | 9/2000 | Fogel |
| 6,159,944 A | | 12/2000 | Fogel |

FOREIGN PATENT DOCUMENTS

| | | |
|---|---|---|
| EP | 0 719 145 B1 | 7/1996 |
| WO | WO 95 06466 A | 3/1995 |
| WO | WO 95/32715 | 12/1995 |
| WO | WO 97/27749 A | 8/1997 |
| WO | WO 98 19672 A | 5/1998 |
| WO | WO 98 27971 A | 7/1998 |

OTHER PUBLICATIONS

Baird, A. A., et al., *Br. J. Pharmacol.* 100, 329–335 (1990).
Carapeti, E A, et al., *Gut* 45:719–722 (1999).
Glavind, E.B., et al., *Am J. Physiol.*, 272(5, Pt. 1), G1075–G1082 (1997).
Gorfine, S. R., *Diseases of the Colon & Rectum*, XP–002084601 "Treatment of Benign Anal Disease with Topical Nitroglycerin", V38, No. 5, pp. 453–457 (1995).
Goyal, R. K., et al., *J. Clin. Invest.*, 52(2), 337–41 (1973).
Heyden, B., et al., *Neurourol. Urodyn.* 14(2), 153–68 (1995).
Rae, MG, et al., *J Physiol*, Jun. 1;493 ( Pt 2);517–27 (1996).
Rattan, S., et al., *American Physiological Society*, G107–G112 (1992).
Salapatek, A M, et al., *Br J Pharmacol Mar.*;123(6):1055–64 (1998).
Salapaetek, A M et al., *Am.. J. Physiol.*, 274(4, Pt. 1), C1145–C1157 (1998).
Szilvassy, Z., et al., *Pharmacol. Res.* 36(2), 129–133 (1997).
JP 10–1441 Tendo Seiyaku KK (Tend–N), *Derwent Patent Summary* (1998).
Winquist, R. J., et al. *Journal of Pharmacology and Experimental Therapeutics*, vol. 248, No. 1 pp. 149–156 (1989).
Benowitz, N. L., "Antihypertensive Agents", *Basic & Clinical Pharmacol.*, Edited by Katzung, Appleton & Lange, pp. 161–162, 1995.
Boushey, H. A., "Bronchodilators & Other Agents Used in Asthma", *Basic & Clinical Pharmacol.*, Edited by Katzung, Appleton & Lange, pp. 310–314, 1995.
Sharp, F. R., "Patient Selection and Treatment Modalities for Chronic Anal Fissure", *Am. J. Surg.*, vol. 171, No. 5, pp. 512–515, 1996.
Kubota, et al., "Membrane properties and the neuro–effector . . . ", Nov. 1998, *J. Smooth Muscle Res.*, vol. 34, pp. 173–184.
Bouvier, et al., "Nervous control of the internal anal sphincter . . . ", Dec. 1981, *J. Phisiol.*, vol. 310, pp. 457–469.
Yamato, et al., "Role of Alpha adrenocepters in opossum internal anal . . . ", abstract, *J. Clin. Invest.*, 1990, vol. 86(2), pp. 424–429.

(List continued on next page.)

*Primary Examiner*—Raymond Henley, III
*Assistant Examiner*—Vickie Kim
(74) *Attorney, Agent, or Firm*—Townsend and Townsend and Crew LLP

(57) ABSTRACT

Compositions and methods for the treatment of anorectal disorders are provided in which certain combinations of NO donors, PDE inhibitors, superoxide ($O_2^-$) scavengers, β-adrenergic agonists, cAMP-dependent protein kinase activators, $α_1$-adrenergic antagonists, L-type $Ca^{2+}$ channel blockers, estrogens, ATP-sensitive $K^+$ channel activators and smooth muscle relaxants are used.

10 Claims, 20 Drawing Sheets

OTHER PUBLICATIONS

T. Morita, et al., "Characterization of Functional Beta–Adrenoceptor Subtypes in Rabbit Urinary Bladder Smooth Muscle," *Tohoku L. exp. Med.*, (Aug. 1986), vol. 149, pp. 389–395.

P. J. Silver, et al., "Cardiovascular activity of WIN 65579, a novel inhibitor of cyclic GMP phosphodiesterase 5,", *Eur. J. Pharmacol.*, (May 22, 1998), 349(2–3):263–268.

F. S. P. Regadas, et al., "Pharmacological Study of the internal anal sphincter in patients with chronic anal fissure," *Br. J. Surg.*, (Jun. 1993), vol. 80, pp. 799–801.

J. Pitt, et al., "The Role of Alpha and Beta adrenoceptors in chronic fissure–in–ano," Program Guide and Abstracts of *The American Society of Colon and Rectal Surgeons*, (May 1999), p. C65.

J. G. Hardman, et al., "Drugs Used in the Treatment of Asthma," Goodman & Gilman's *The Pharmacological Basis of Therapeutics, 9$^{th}$ ed.*, McGraw–Hill, NY, (1996), pp. 672–682.

M. Li, et al., "Minoxidil–Induced Hair Growth is Mediated by Adenosine in Cultured Dermal Papilla Cells: Possible Involvement of Sulfonylurea Receptor 2B as a Target of Minoxidil," *The Journal of Investigative Dermatology*, vol. 117, No. 6, (2002), pp. 1594–1600.

A. Crema, et al., "Purine receptors in the guinea–pig international anal sphincter," *Br. J. Pharmac.*, vol. 78, (1983), pp. 599–603.

S. Chakder and S. Rattan, "Involvement of cAMP and cGMP in relaxation of internal anal sphincter by neural stimulation, VIP, and NO," *The American Physiological Society*, (1993), pp. G702–G707.

G. Burnstock, et al., "A comparison of the excitatory and inhibitory effects of non–adrenergic, non–cholinergic nerve stimulation and exogenously applied ATP on a variety of smooth muscle preparations from different vertebrate species," *Br. J. Pharmac.*, vol. 46, (1972), pp. 234–242.

I. Biaggioni, et al., "Caffeine and Theophylline as Adenosine Receptor Antagonists in Humans," *The Journal of Pharmacology and Experimental Therapeutics*, vol. 258, No. 2, (1991), pp. 588–593.

D. E. Burleigh, "Non–cholinergic, non–adrenergic inhibitory neurons in human internal anal sphincter muscle," *J. Pharm, Pharmacol.*, vol. 35, (1983), pp. 258–260.

R. B. Meyer and J. P. Miller, "Minireview, Analogs of Cyclic AMP and Cylic GMP: General Methods of Synthesis and the Relationship of Structure to Enzymic Activity," *Life Sciences*, vol. 14, (1974), pp. 1019–1040.

B. Heesen and J. De Mey, "Effects of cyclic AMP–affecting agents on contractile reactivity of isolated mesenteric and renal resistance arteries of the rat," *Br. Pharmacol.*, vol. 101, (1990), pp. 859–1040.

S. Rattan and R. Shah, "Influence of purinoceptors' agonists and antagonists on opossum internal anal sphincter," *The American Physiological Society*, (1988), pp. G389–394.

S. Mirzazadeh, "Cyclic Nucleotide Content of the Rat Anococcygeus During Relaxations Induced by Drugs or by Non–adrenergic, Non–cholinergic Field Stimulation," *J. Pharm. Pharmacol.*, (1991), vol. 43, pp. 247–257.

B. Frencker and T. Ihre, "Influence of autonomic nerves on the internal anal sphincter in man," *Gut*, vol. 17, (1976), pp. 306–312.

A. Fujita, et al., "Activation of ATP–sensitive K+ channels by ADP and K+ channel openers; homology model of sulfonylurea receptor carboxyl–termini," *Nippon Yakurigaku Zasshi*, vol. 118, (Sep. 2001), pp. 177–86.

\* cited by examiner

COMPOSITIONS AND METHODS FOR THE TREATMENT OF ANORECTAL DISORDERS

CROSS-REFERENCES TO RELATED APPLICATIONS

This application claims priority under 35 U.S.C. 119(e) of U.S. patent application Ser. No. 60/222,267, filed Jul. 31, 2000. This application also is a Continuation-In-Part and claims priority to U.S. patent application Ser. No. 09/460,306, filed Dec. 13, 1999; U.S. patent application Ser. No. 09/595,390 filed on Jun. 14, 2000; and U.S. patent application Ser. No. 09/769,621 filed Jan. 23, 2001 which each claim priority from U.S. Provisional Application No. 60/112,325, filed Dec. 14, 1998; U.S. Provisional Application No. 60/139,916, filed Jun. 17, 1999 and U.S. Provisional Application No. 60/155,318, filed Sep. 21, 1999. The disclosure of each of the above priority documents is incorporated herein by reference in its entirety.

STATEMENT AS TO RIGHTS TO INVENTIONS MADE UNDER FEDERALLY SPONSORED RESEARCH OR DEVELOPMENT

This invention was made with government support under Grant Number 1 R43 DK 56563-01 awarded by the National Institutes of Health, National Institute of Diabetes and Digestive and Kidney Diseases. The Government has rights in certain aspects of the invention.

REFERENCE TO A "SEQUENCE LISTING," A TABLE, OR A COMPUTER PROGRAM LISTING APPENDIX SUBMITTED ON A COMPACT DISK.

NOT APPLICABLE

BACKGROUND OF THE INVENTION

This invention is directed to compositions and methods for treating anorectal disorders such as anal fissures, anal ulcer, hemorrhoidal diseases and levator spasm by administering to an appropriate anal area (for example, the internal anal canal) of a subject in need of such treatment an agent or combination of agents which relaxes the internal anal sphincter muscle. More specifically, this invention describes compositions and methods for treating anorectal disorders with agents which induce an increase in cyclic nucleotides in the anal sphincter muscle or which mimic the actions of cyclic nucleotides or reduce intracellular calcium concentrations in the affected anal sphincter muscle tissue, thereby reducing anal sphincter hypertonicity and/or spasm in patients afflicted with such disorders.

In general, anal fissure (fissure-in-ano), anal ulcer, hemorrhoidal diseases, and levator spasm (proctalgia fugax) are relatively common benign conditions of the anorectal area which affect subjects, including humans, of all ages, races, and sexes. While hemorrhoids and anal fissures do not garner the attention given to life threatening diseases, they are responsible for considerable suffering and disability, affecting over 26 million people in the U.S., Europe, and Japan.

An anal fissure or ulcer is a tear or ulcer of the mucosa or lining tissue of the distal anal canal. An anal fissure or ulcer can be associated with another systemic or local disease, but is more frequently present as an isolated finding. The typical idiopathic fissure or ulcer is confined to the anal mucosa and usually lies in the posterior midline, distal to the dentate line. An individual with an anal fissure or ulcer frequently experiences anal pain and bleeding, the pain being more pronounced during and after bowel movements.

Hemorrhoids are specialized vascular areas lying subjacent to the anal mucosa. Symptomatic hemorrhoidal diseases are manifested by bleeding, thrombosis and/or prolapse of the hemorrhoidal tissues. Commonly, internal hemorrhoidal tissue bulges into the anal canal during defecation and results in bleeding and pain. As the tissue enlarges, further bleeding, pain, prolapse and thrombosis can ensue. The thrombosis of hemorrhoids is yet another cause of bleeding and pain.

Levator spasm is a condition affecting women more frequently than men. This syndrome is characterized by spasm of the levator ani muscle, a portion of the anal sphincter complex. The patient suffering from levator spasm may experience severe, episodic rectal pain. A physical exam may reveal spasm of the puborectalis muscle and pain may be reproduced by direct pressure on this muscle. Bleeding is normally not associated with this condition.

Hemorrhoids are the most prevalent anorectal disorder and are the most common cause of hematochezia (i.e., passage of bloody stools). Hemorrhoidal disease is the consequence of distal displacement of the anal cushions, which normally play an important role in continence. The causes of hemorrhoids are not known. The most consistently demonstrated physiological abnormality is increased resting anal pressure (Hancock B. D., *Br J Surg* 64(2):92–5 (1975); Loder, P. B., *Br J Surg* 81(7):946–54 (1994)). Patients with non-prolapsing hemorrhoids appear to have higher anal pressures than those with prolapsing hemorrhoids (Arabi, Y. et al., *Am J Surg* 134(5):608–10 (1977); Sun, W. M. et al., *Br J Surg* 77(4): 458–62, (1990)), although the therapeutic implications of this observation remain unclear. Treatment is dependent on the degree of hemorrhoid prolapse and symptoms. Most cases (first- and second-degree hemorrhoids) generally respond to conservative medical treatment (e.g., dietary changes, sitz baths) or non-surgical procedures (e.g., rubber band ligation). Acutely thrombosed external hemorrhoids are usually characterized by severe anal pain, and internal anal sphincter hypertonia may play a role in the etiology of this pain (Gorfine, S. R., *Dis Colon Rectum* 38(5): 453–7 (1995)). Surgical excision of symptomatic thrombosed external hemorrhoids is indicated within 48 to 72 hours of the onset of pain. Post-hemorrhoidectomy pain is severe, disproportionate to the surgery itself, and requires the use of narcotic analgesics, which unfortunately complicate recovery by causing constipation. Anal dilatation and lateral internal sphincterotomy as treatments to reduce anal sphincter pressure in hemorrhoids have been used successfully, both as stand alone procedures and in conjunction with hemorrhoidectomy (Keighley, M. R. et al., *Br Med J* J2(6196):967–9 (1979); Schouten W. R. et al., *Dis Colon Rectum* 28(12), 869–72 (1986); Galizia et al., *Eur J Surg* 166(3):223–8 (2000)).

Others have reported that the addition of lateral internal sphincterotomy to routine hemorrhoidectomy is unnecessary and carries the added risk of incontinence (Mathai, V. et al., *Br J Surg.* 83(3):380–2 (1996)).

Anal fissure is one of the most common causes of anorectal pain. Anal fissures are tears in the mucosa of the distal anal canal, usually along the posterior midline. The exact causes of anal fissures remain unknown. They are often associated with trauma, e.g., passage of a hard stool, but can also occur during bouts of diarrhea, childbirth, or ulceration of a hemorrhoid (Lund, J. N. et al., *Br J Surg.* 83(10): 1335–44 (1996)). The most common symptom is pain at defecation, which can be quite severe and last for a variable time afterwards. The pain is chiefly due to an intense spasm of the internal anal sphincter muscle. Most anal fissures are adequately treated with sitz baths, stool softeners, and analgesics. Approximately 60% of acute anal fissures will heal within three weeks using this treatment regimen. Acute anal fissures, which do not heal, become chronic anal fissures or anal ulcers. Hypertonicity of the internal anal sphincter muscle and mucosal ischemia are thought to play an important role in the pathogenesis of chronic anal fissures (Schouten W. R. et al., *Dis Colon Rectum* 37(7):664–9 (1994); Lund, J. N. et al., *Br J Surg* 83(10): 1335–44 (1996)). Anodermal blood flow at the posterior midline is less than other regions of the anal canal, and perfusion of the posterior mucosa is inversely related to anal pressure. Chronic anal fissures are typically not responsive to conservative medical therapy. Current treatments are therefore directed at relieving sphincter spasm, and include anal dilatation (under anesthesia), or more commonly, lateral sphincterotomy of the internal anal sphincter. Healing occurs following surgical sphincterotomy in 95% of cases. Successful sphincterotomy (or anal dilatation) is associated with a significant decrease in intra-anal pressure and increase in anodermal blood flow (Lund, J. N. et al., *Br J Surg* 83(10): 1335–44, (1996); Schouten W. R. et al., *Scan J Gastroenterol. Suppl* 218: 78–81 (1996)). However, up to 35% of patients may experience some form of incontinence following the surgical procedure (Sharp, F. R., *Am J Surg* 171(5):512–5 (1996)). Incontinence of stool and flatulence is a humiliating disability with numerous social, medical, and financial implications. There is clearly a large unmet medical need to develop effective, non-surgical treatments for anal fissure and other colorectal conditions, including acute hemorrhoidal disease, hemorrhoidectomy pain, proctalgia fugax, and severe constipation. Considerable recent progress has been made in the understanding of anorectal physiology and pharmacology. These new insights provide important implications and opportunities for the pharmacological management of colorectal disorders.

Sphincters are circular groups of smooth muscle that control the orifices of hollow organs. They are present throughout the gastrointestinal tract and control the passage of materials through this system of the body. When constricted, sphincters close orifices leading to or from the hollow organs, such as the stomach, intestine, rectum, etc. In order for the orifice to open, the sphincter must relax. The, sphincter that closes the anus (sphincter ani) consists of two sphincter muscle groups. The external anal sphincter is a thin flat plane of striated muscle fibers adherent to the integument surrounding the margin of the anus. It is innervated by motor neurons and is under voluntary control. The internal anal sphincter (IAS) is a ring of smooth muscle that surrounds the anal canal and is formed by a specialized aggregation of involuntary circular smooth muscle fibers of the intestine. The IAS is largely responsible for resting anal sphincter pressure and continence which is maintained by intrinsic myogenic tone and regulated by both intrinsic and extrinsic innervation from the autonomic nervous system (Penninckx, F. et al., *Baillieres Clin Gastroenterol* 6(1) 193–214 (1992); Speakman, C. T. *Eur J Gastroenterol Hepatol* 9(5):442–6 (1997)).

The IAS smooth muscle constantly generates rhythmic electrical slow waves, but no action potentials. The slow waves are linked to calcium fluxes via voltage-dependent, L-type calcium channels that are responsible for mechanical force generation and contraction of the sphincter. Accordingly, several calcium channel antagonists, including diltiazem and nifedipine, have been documented to reduce anal pressure in man (Jonard et al., *Lancet* 1(8535): 754 (1987); Chrysos, E. et al., *Dis Colon Rectum* 39(2): 212–6 (1996); Antropoli, C. et al., *Dis Colon Rectum* 42(8):1011–5 (1999); Carapeti, E. A. et al., *Gut* 45(5) 719–722 (1999); Carapeti, E. A. et al., *Br J Surg* 86(2):267–70 (1999), and in several reports, to heal chronic anal fissures (Cook, T. A. et al., *Br J Surg* 86(10):1269–73 (1999); Brisinda, G. et al., *Br J Surg* 87(2): 251 (2000)).

Sympathetic innervation of the IAS, supplied by the hypogastric nerves, is primarily excitatory and functions to enhance myogenic tone through the action of norepinephrine on smooth muscle $\alpha_1$-adrenergic receptors (Frenckner, B., et al., *Gut* 17(4):306–12 (1976); Speakman, C. T. et al., *Dig Dis Sci* 38(11)1961–9 (1993)). The $\alpha_1$-adrenergic receptor antagonists phentolamine and indoramin reduce anal canal pressure when administered to healthy volunteers or patients with chronic anal fissures (Speakman, C. T., *Eur J. Gastroenterology* 9(5):442–6 (1997); Pitt, J. et al., *Dis Colon Rectum* 43(6)800–803 (2000)). Conversely, the α-receptor agonists methoxamine and phenylephrine increase anal pressure (Speakman, C. T. 1997 supra; Carapeti, E. A. et al., *Br J Surg* 86(2):267–70 (1999)). Low anal pressure is associated with incontinence (Speakman, C. T. *Gastroenterology* 9(5):442–6 (1997)). Speakman, C. T. et al., (Speakman, C. T. et al., *Dig. Dis Sci.* 38(11):1961–9 (1993)) reported that the IAS of incontinent patients exhibit reduced sensitivity to norepinephrine. Although the α-adrenergic receptor population is dominant, β-adrenergic receptors are also present on human IAS, and mediate relaxation (Parks, A. G., et al., *Gut* 10(8):674–7 (1969); Burleigh, D. E., et al., *Gastroenterology* 77(3): 484–90, (1979). The contractile response of the IAS to norepinephrine can be converted to relaxation in the presence of selective α-receptor blockade, both in vitro and in normal human volunteers (Burleigh, D. E., et al., *Gastroenterology* 77(3): 484–90, (1979); Speakman, C. T., *Eur J Gastroenterology* 9(5):442–6 (1997)). Regadas and colleagues (Regadas, F. S. et al., *Br J Surg* 80(6):799–801 (1993)) demonstrated that isolated IAS strips from chronic anal fissure patients were significantly more sensitive to the relaxant effects of the β-adrenergic agonist isoproterenol than control tissues, whereas no differences were noted in the contractile responses to phenylephrine and potassium chloride (a membrane depolarizing agent). However, it remains to be determined whether β-adrenergic agonists offer disease-specific advantages for the treatment of chronic anal fissure.

The IAS relaxes in response to rectal distention (the rectoanal inhibitory reflex). The nerves mediating the rectoanal inhibitory reflex lie entirely within the wall of the gut (enteric inhibitory neurons), and descend from the rectum to the IAS. Electrical field stimulation (EFS) mimics the effects of intrinsic nerve stimulation on isolated smooth muscle strips. IAS strips are relaxed by EFS, an effect that is abolished by the neurotoxin tetrodotoxin, but is unaffected by antagonists of the classical neurotransmitters, acetylcholine or norepinephrine. The inhibitory nerves are thus classified as non-adrenergic, non-cholinergic (NANC) nerves. Adenosine triphosphate (ATP) and vasoactive intestinal peptide (VIP) were first suggested as NANC neurotransmitter candidates since they mimicked the relaxation elicited by electrical stimulation of motor nerve fibers (Burnstock, G. et al., *Br J Pharmacol.* 46(2):234–42 (1972); Bitar, K. N. et al., *Science* 216(4545): 531–3 (1982)). However, ATP and VIP, either separately or together, could not account for all inhibitory neurotransmission in gastrointestinal smooth muscle, and their roles have not been established in man (Burleigh, D. E. et al., *Gastroenterology* 77(3): 484–90 (1979); Burleigh, D. E., *J Pharm Pharmacol* 35(4):258–60 (1983); Brookes, S. J., *J Gastroenterol Hepatol* 8(6):590–603 (1993).

Recent studies indicate that NO plays an important role in NANC nerve mediated relaxation of the IAS. In an animal model, Rattan, S. et al., (Rattan, S. et al., *Am J Physiol* 262 (1 Pt 1):G107–12 (1992) demonstrated that IAS relaxation associated with the rectoanal reflex (induced by rectal balloon distention), or neural stimulation, was blocked by inhibition of NO synthase (NOS) with L-NNA [$N^5$-(nitroamidino)-L-2,5-diaminopentanoic acid], but not with D-NNA. Block of the rectoanal reflex by L-NNR was reversed by L-arginine in a stereospecific manner, implicating NO or NO-like substances as mediators of NANC nerve mediated IAS relaxation. NO was shown to directly relax the IAS in a concentration-dependent manner in vitro, mimicking the effect of NANC nerve stimulation by EFS. NANC nerve-mediated relaxation of IAS strips in vitro was blocked by inhibition of NO synthase with L-NNA, and the block was reversed by L-arginine, but not D-arginine (Rattan, S. et al., *Am J Physiol* 262 (1 Pt 1):G107–12, (1992) and Rattan, S. et al., *Gastroenterology* 103(1):43–50 (1992)). Similar observations have been made using isolated muscle strips of human IAS (Burleigh *Gastroenterology* 102(2): 679–83 (1992); O'Kelly, T. J. et al., *Br J Surg* 80(10): 1337–41, (1993)). The direct release of NO following NANC nerve stimulation of opossum IAS strips was demonstrated using a specific chemiluminescence detection method (Chakder, S. et al., *Am J Physiol.,* 264 (4 Pt 1)G702–7 (1993)). O'Kelly (O'Kelly, T. J. et al., *Dis Colon Rectum* 37(4): 35–7 (1994)) recently demonstrated the presence of NOS in neurons of the myenteric plexus that project throughout the IAS and lay in close proximity to smooth muscle cells. In Hirschsprung's disease, a condition in which the rectoanal reflex is absent, NOS containing nerves were absent from the non-relaxing segment, but present in the normal segment of the gut (O'Kelly, T. J. et al., *J Pediatric Surgery* 29(2): 294–9 (1994)). These observations fulfill most of the criteria for NO as an inhibitory mediator or neurotransmitter.

A number of potent vasodilators and smooth muscle relaxants are known to chemically release NO on or within target cells, and thus are known as NO donors. Some NO donors, e.g., nitroglycerin, are widely used therapeutically as coronary vasodilators to treat heart disease. In keeping with the role of NO as an inhibitory neurotransmitter mediating relaxation of the IAS, NO donors are beginning to be explored clinically as drugs to treat anal disorders associated with IAS hypertonicity. Significantly, nitroglycerin (Gorfine, S. R., *Dis Colon Rectum,* 38(5):453–6 (1995); Watson, S. J. et al., *Br J Surgery* 83(6):771–5, 1996; Lund, J. N. et al., *Lancet* 349: 9044 (1997)) and isosorbide dinitrate have been used to effect a reversible chemical sphincterotomy in patients with chronic anal fissure. These drugs reduce maximal resting anal pressure and, improve anodermal blood flow, reduce pain, and heal fissures in a majority of the patients. Nitroglycerin has also been shown to reduce the throbbing pain of acute hemorrhoidal thrombosis and proctalgia fugax (Gorfine, S. R., *Dis Colon Rectum* 38(5):453–6 (1995); Lowenstein, B. et al., *Dis Colon Rectum* 41(5):667–8 (1998)).

U.S. Pat. Nos. 5,504,117 and 5,693,676 describe the use of NO donors for the treatment of anorectal conditions. However, the development of adverse side effects such as the development of headaches has limited the use of NO donors in stand alone therapy, especially at higher doses.

One problem associated with topical nitroglycerin therapy, which may limit its effectiveness, is the incidence of headache, particularly at higher doses (Palazzo, F. F. et al., *J R Coll Surg Edinb* 45(3):168–70 (2000)). The headache is presumably due to systemic effects of nitroglycerin and is generally transient, but can affect patient compliance. There is a need for treatment methods strategies which enhance the local effect of nitroglycerin and minimize its systemic side effects. A second potential problem of nitrates is the development of drug tolerance, a problem well documented for nitrate therapy in cardiovascular disease (Fung, H. L., et al., *Cardiovasc Drugs Ther* 8(3):489–99, (1994)). Tolerance, if present, would limit the ability of nitroglycerin to produce a sustained relaxation of the IAS, which may be necessary for healing particularly refractory chronic anal fissures.

There is clearly a significant need for other non-surgical treatments of anorectal disorders, including, for example, anal fissures and other anorectal conditions caused by anal sphincter spasm and or hypertonicity, including acute hemorrhoidal diseases and proctalgia fugax.

There is thus a need for alternative methods and compositions for reducing anal sphincter pressure that complement or supplant nitroglycerin.

The use of a topical or intra-rectal pharmaceutical preparation that complements or supplants nitroglycerin for the treatment of chronic anal fissures and other anorectal disorders can provide the first effective alternative to surgery for this painful disorder.

BRIEF SUMMARY OF THE INVENTION

In one aspect, the present invention provides compositions for the treatment of anorectal disorders comprising a nitric oxide donor in combination with a second agent (typically one which modulates levels of cAMP or cGMP). The second agent can be a phosphodiesterase type V (PDE V) inhibitor, a phosphodiesterase type II (PDE II) inhibitor, a phosphodiesterase type IV (PDE IV) inhibitor, a nonspecific PDE inhibitor, a β-adrenergic agonist, a cAMP-dependent protein kinase activator, an estrogen or estrogen-like compound, or an $\alpha_1$-adrenergic antagonist. The agent can also be a superoxide anion ($O_2^-$) scavenger, an ATP-sensitive $K^+$ channel activator, a sympathetic nerve terminal destroyer, or a smooth muscle relaxant, although these agents do not directly modulate either cAMP or cGMP levels. The present invention further provides methods of using these compositions.

In another aspect, the present invention provides compositions for the treatment of anorectal disorders comprising a phosphodiesterase inhibitor, preferably a PDE II inhibitor, a PDE IV inhibitor or a PDE V inhibitor, either alone or in combination with another agent selected from β-adrenergic receptor agonists, $\alpha_1$-adrenergic antagonists, estrogens, L-type $Ca^{2+}$ channel blockers, ATP-sensitive $K^+$ channel activators, or smooth muscle relaxants, in combination with a pharmaceutically acceptable carrier. The present invention also provides methods of using these compositions.

In another aspect, the present invention provides compositions for the treatment of anorectal disorders comprising a β-adrenergic receptor agonist, preferably a $\beta_2$- or $\beta_3$-adrenergic receptor agonist, either alone or in combination with another agent selected from cAMP-hydrolyzing PDE inhibitors (e.g., a PDE IV inhibitor), nonspecific PDE inhibitors, $\alpha_1$-adrenergic antagonists, estrogens or estrogen-like compounds, L-type $Ca^{2+}$ channel blockers, or ATP-sensitive $K^+$ channel activators, and methods of using those compositions.

In yet another aspect, the present invention provides compositions for the treatment of anorectal disorders comprising an ATP-sensitive K+ channel activator, either alone or in combination with another agent selected from cAMP-dependent protein kinase activators, $\alpha_1$-adrenergic antagonists, estrogens, L-type $Ca^{2+}$ channel blockers, or smooth muscle relaxants, and methods of using those compositions.

In still another aspect, the present invention provides compositions for the treatment of anorectal disorders comprising an $\alpha_1$-adrenergic antagonist, either alone or in combination with another agent selected from cAMP-hydrolyzing PDE inhibitors (preferably a PDE IV inhibitor) or smooth muscle relaxants, and methods of using those compositions.

In another aspect, the present invention provides compositions for the treatment of anorectal disorders comprising $\beta_2$-adrenergic agonists, either alone or in combination with another agent. Methods for the use of these compositions are also provided. In one group of embodiments, the $\beta_2$-adrenergic agonists are used alone. In a preferred embodiment, the $\beta_2$-adrenergic agonists is combined with a phosphodiesterase inhibitor. In another embodiment, the $\beta_2$-adrenergic agonists are combined with one or more other IAS relaxing agents.

In another aspect, the present invention provides compositions for the treatment of anorectal disorders comprising adenosine receptor antagonists, either alone or in combination with another agent. Methods for the use of these compositions are also provided. In one group of embodiments, adenosine receptor antagonists are used alone. In another group of embodiments, the adenosine receptor antagonists are combined with at least one other IAS relaxing agent.

In another aspect, the present invention provides compositions for the treatment of anorectal disorders comprising cyclic nucleotide-dependent protein kinase activators, either alone or in combination with another agent. Methods for the use of these compositions are also provided. In one group of embodiments, cGMP-dependent protein kinase activators are used alone. In another group of embodiments, nonspecific cyclic nucleotide-dependent protein kinase activators are used alone. In yet another group of embodiments, nonspecific cyclic nucleotide-dependent protein kinase activators are used in combination with smooth muscle relaxants. In still another group of embodiments, cAMP-dependent protein kinase activators are provided in combination with L-type $Ca^{2+}$ channel blockers.

In yet another aspect, the present invention provides a composition for the treatment of anorectal disorders comprising a methylxanthine compound. In preferred embodiments, the compound is theophylline or dyphylline. In still another embodiment, the methylxanthine compound is used alone. In still another embodiment, the methylxanthine compound is combined with another IAS relaxing agent.

In yet another aspect, the present invention provides compositions for the treatment of anorectal disorders comprising an estrogen or other estrogenic compound, either alone or in combination with another agent. Methods for the use of these compositions are also provided. In one group of embodiments, estrogenic compounds are used alone. In another group of embodiments, the estrogenic compounds are used in combination with a second agent selected from phosphodiesterase inhibitors, β-adrenergic receptor agonists, $\alpha_1$-adrenergic antagonists, L-type $Ca^{2+}$ channel blockers, ATP-sensitive K+ channel activators, or smooth muscle relaxants, in combination with a pharmaceutically acceptable carrier. The present invention further provides methods of using these compositions.

Where the compounds discussed above act through mechanisms distinctly different from nitroglycerin, they can be used to complement nitroglycerin therapy, or as stand alone products.

As noted above, methods of treating anorectal disorders are also provided herein. The methods of the invention comprise administering to a subject a suitable formulation of one or more of the compositions above. In related methods, treatment is carried out by administration of two or more agents in sequence, either by the same route of administration or by different routes of administration.

DETAILED DESCRIPTION OF THE INVENTION

Figure 1:
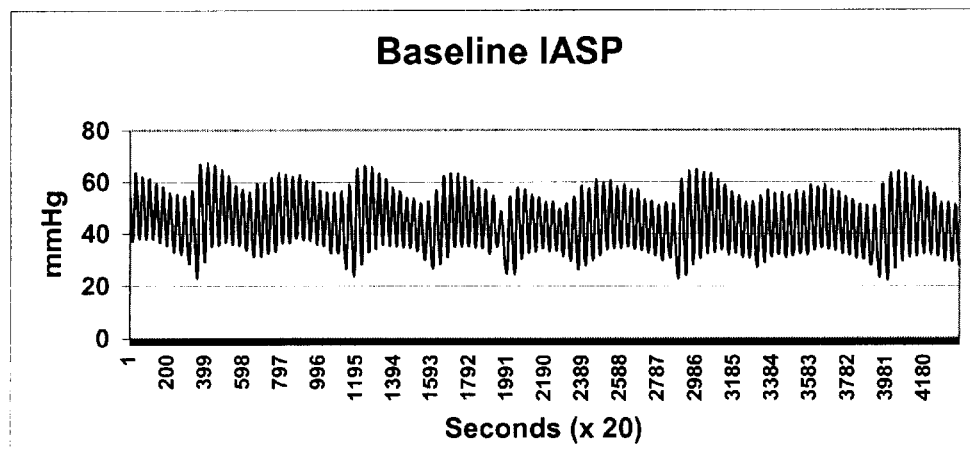
FIG. 1 illustrates a typical waveform pattern for resting IASP in a rat under conditions of a control experiment.

Abbreviations and Definitions cAMP, cyclic adenosine monophosphate; cGMP, cyclic guanosine monophosphate; NO, nitric oxide; NTG, nitroglycerin; SOD, superoxide dismutase; PDE, phosphodiesterase; IASP, internal anal sphincter pressure; Rp-cAMPS, Rp-Adenosine-3',5'-cyclic monophosphorothioate; Sp-cAMPS, Sp-Adenosine-3',5'-cyclic monophosphorothioate; 8-CPT cAMP, 8-(4-Chlorophenylthio)-adenosine-3',5'-cyclic monophosphate, sodium salt; Sp-5,6-DCI-cBiMPS, Sp-5,6-dichloro-1-b-D-ribofuranosylbenzimidazole-3',5'-monophosphorothioate; Dibutyryl-cAMP, N6,2'-O-Dibutyryladenosine-3',5'-cyclic monophosphate, sodium salt monohydrate; Sp-8-pCPT-cGMPS, Sp-8-(4-Chlorophenylthio)-quanosine-3',5'-cyclic monophosphate, sodium salt; 8-Bromo-cGMP, 8-Bromoguanosine-3',5'-cyclic monophosphate, sodium salt; Rp-8-Br-cGMPS, Rp-8-Bromoguanosine-3',5'-cyclic monophosphorothioate, sodium salt; Dibutyryl-cGMP, N2,2'-O-Dibutyrylguanosine-3',5'-cyclic monophosphate, sodium salt; EHNA, erythro-9-(2-Hydroxy-3-nonyl)adenine HCl; IBMX, 3-Isobutyl-1-methylxanthine; MY-5445, 1-(3-Chlorophenylamino)-4-phenylphthalazine; Ro 20-1724, 4-(3-Butoxy-4-methoxybenzyl)-2-imidazolidinone; MBCQ, 4-((3,4-(Methylenedioxy) benzyl)amino)-6-chloroquinazoline.

Unless defined otherwise, all technical and scientific terms used herein have the same meaning as commonly understood by those of ordinary skill in the art to which this invention belongs. The following references provide one of skill with a general definition of many of the terms used in this invention: Singleton et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); and Hale & Marham, THE HARPER COLLINS DICTIONARY OF BIOLOGY (1991). As used herein, the following terms have the meanings ascribed to them unless specified otherwise. Although any methods and materials similar or equivalent to those described herein may be used in the practice or testing of the present invention, the preferred methods and materials are described. For purposes of the present invention, the following terms are defined below.

The terms "treatment", "therapy" and the like include, but are not limited to, changes in the recipient's status. The changes can be either subjective or objective and can relate to features such as symptoms or signs of the disease or condition being treated. For example, if the patient notes decreased itching, reduced bleeding, reduced discomfort or decreased pain, then successful treatment has occurred. Similarly, if the clinician notes objective changes, such as by histological analysis of a biopsy sample, then treatment has also been successful. Alternatively, the clinician may note a decrease in the size of lesions or other abnormalities upon examination of the patient. This would also represent an improvement or a successful treatment. Preventing the deterioration of a recipient's status is also included by the term. Therapeutic benefit includes any of a number of subjective or objective factors indicating a response of the condition being treated as discussed herein.

"Drug", "pharmacological agent", "pharmaceutical agent", "active agent", and "agent" are used interchangeably and are intended to have their broadest interpretation as to any therapeutically active substance which is delivered to a living organism to produce a desired, usually beneficial effect.

"Pharmaceutically-acceptable" or "therapeutically-acceptable" refers to a substance which does not interfere with the effectiveness or the biological activity of the active ingredients and which is not toxic to the hosts, which may be either humans or animals, to which it is administered. "Therapeutically-effective amount" refers to the amount of an active agent sufficient to induce a desired biological result. That result may be alleviation of the signs, symptoms, or causes of a disease, or any other desired alteration of a biological system. The term "therapeutically effective amount" is used herein to denote any amount of the formulation which causes a substantial improvement in a disease condition when applied to the affected areas repeatedly over a period of time. The amount will vary with the condition being treated, the stage of advancement of the condition, and the type and concentration of formulation applied. Appropriate amounts in any given instance will be readily apparent to those skilled in the art or capable of determination by routine experimentation.

The term "anorectal area" is defined herein to include both the anus and the rectum region of a mammal. More particularly, the term includes the internal anal canal, the external anus and the lower rectum.

"Hypertonicity" refers to being in state of greater than normal muscular tension or of incomplete relaxation.

The term "cyclic nucleotide" refers to cyclic adenosine monophosphate and cyclic guanosine monophosphate.

The term "modulation" refers to any systematic variation or graded change in a characteristic (e.g. frequency, concentration, amplitude, effectiveness, etc.) of a sustained oscillation sufficient to affect a biological function. The term "change" includes an increase or decrease in the characteristic.

The term "subject" as used herein includes any animal, such as a mammal, including a human.

The term "anorectal disorder" includes any disorder associated with an anal rectal disease, including an acute or chronic anal fissure, an internally or externally thrombosed hemorrhoid, a hemorrhoidal disease, a disorder associated with endoscopic hemorrhoidal ligation or pain caused by such ligation, levator spasm, constipation, and other anorectal disorder caused by hypertonicity or spasm of the anal sphincter muscle. The term also refers to post-surgical pain associated with hemorrhoidectomy or other anorectal surgery that leads to intense anal spasms. The term "anal fissure" is also referred to as "anal rhagades" and spasms of the anal sphincter are also referred to as "rectal tenesmus." Additionally, the term is meant to include pain which can be associated with any of the above disorders or conditions.

The terms "signs, symptoms and causes of anorectal disease" and "signs and symptoms of anorectal disease" include, but are not limited to, anal sphincter hypertonicity; anal and rectal ischemia, itching, inflammation, pain or bleeding; thrombosed or prolapsed hemorrhoidal tissue; spasticity of the levator ani muscle, spasm of the puboretalis muscle or anal sphincter muscles, and linear or ischemic ulcers or crack-like sores in the anal canal or on the margin of the anus.

The term "desirable therapeutic effects" in the treatment of anorectal diseases and conditions includes, but is not limited to, anal sphincter relaxation; reduction of anal sphincter pressure; maintenance of reduced anal sphincter pressure; reduction or elimination of ischemia, itching, inflammation, pain, bleeding, or muscle spasm; restoration or improvement of anoderm blood flow; dilation of blood vessels in the anus and rectum; and partial or complete healing of linear or ischemic ulcers or crack-like sores in the anal canal or on the margin of the anus.

The terms "potassium channel opener" and "potassium channel activator" refer generally to a class of drugs that cause an increased flow of potassium ions from inside an electrically excitable cell to outside the cell via a membrane of the cell which has at least one potassium channel. Potassium channel opener activity may be observed by measuring a hyperpolarization of the cell membrane potential (i.e. a more negative membrane potential) caused by an increase in the flow of potassium ions from inside a cell to outside the cell via a potassium channel in the cell membrane.

The term "pharmaceutical composition" means a composition suitable for pharmaceutical use in a subject, including an animal or human. A pharmaceutical composition generally comprises an effective amount of an active agent and a pharmaceutically acceptable carrier.

The term "pharmaceutically acceptable carrier" encompasses any of the standard pharmaceutical carriers, buffers and excipients, including phosphate-buffered saline solution, water, and emulsions (such as an oil/water or water/oil emulsion), and various types of wetting agents and/or adjuvants. Suitable pharmaceutical carriers and their formulations are described in REMINGTON'S PHARMACEUTICAL SCIENCES (Mack Publishing Co., Easton, 19th ed. 1995). Preferred pharmaceutical carriers depend upon the intended mode of administration of the active agent. Typical modes of administration are described below.

The term "effective amount" means a dosage sufficient to produce a desired result. The desired result may comprise a subjective or objective improvement in the recipient of the dosage.

A "prophylactic treatment" is a treatment administered to a subject who does not exhibit signs of a disease or exhibits only early signs of a disease, wherein treatment is administered for the purpose of decreasing the risk of developing pathology.

A "therapeutic treatment" is a treatment administered to a subject who exhibits signs of pathology, wherein treatment is administered for the purpose of diminishing or eliminating those pathological signs.

The term "appropriate anal area" means any area or tissue of the anus or sphincter that is affected by or subject to anal disorder or disease, including, for example, the external or internal anus, the external or internal anal sphincter, anal sphincter muscle, or external or internal anal canal.

As used herein, the term "NO donor" refers to any organic or inorganic compound that can deliver nitric oxide in a physiologic setting. Also included are those compounds that can be metabolized in vivo into a compound which delivers nitric oxide (e.g., a prodrug form of a NO donor, or a binary NO generating system).

General

A promising new approach for treating anal disorders is the topical application of a nitric oxide (NO) donor to an appropriate anal area. Nitric oxide has been shown to bring about a concentration-dependent reduction in the resting tension of internal sphincter smooth muscle strips in vitro (Rattan, S. et al., *Am J Physiol* 262:G107–112 (1992)), and NO donors (e.g., nitroglycerin, isosorbide dinitrate, isosorbide mononitrate, and L-arginine) have been shown to reduce anal pressure in humans. Schouten, W. R. et al., "Pathophysiological aspects and clinical outcome of intra-anal application of isosorbide dinitrate in patients with chronic anal fissure," *Gut* 39:465–9 (1996); Farid, M., *Br J Surg* 84:1 (1997); and Hechtman, H. B. et al., *Arch. Surg* 131:775–778 (1996). NO has also been shown to mediate adaptive relaxation of other sphincters in the gastrointestinal tract including the lower esophageal sphincter (Conklin et al., *Gastroenterology* 104:1439–1444 (1993); Tottrup et al., *Br J Pharmacol* 104:113–116 (1991)), pyloric sphincter (Bayguinov et al., *Am J Physiol* 264:G975–983 (1993), sphincter of Oddi (Mourelle et al., *Gastroenterology* 105:1299–1305 (1993)), and the ileocolic sphincter (Ward et al., *Br J Pharmacol* 105:776–782 (1992)). It is thought that NO or NO-like substances serve as important control mechanisms for the general phenomenon of gastrointestinal adaptive relaxation.

Despite the initial promise of NO donors, tachyphylaxis has been observed for members of this class of agents. Surprisingly, the present invention provides compositions which are useful to overcome side effects and problems associated with the current therapies.

Description of the Embodiments

NO Donors in Combination with a Second Agent

In one aspect, the present invention provides compositions for the treatment of anal disorders comprising a nitric oxide donor in combination with a second agent which modulates levels of cAMP or cGMP. In one group of embodiments the second agent is a phosphodiesterase type V (PDE V) inhibitor. In another group of embodiments the second agent is a phosphodiesterase type IV (PDE IV) inhibitor. In another group of embodiments the second agent is a phosphodiesterase type II (PDE II) inhibitor. In another group of embodiments the second agent is a nonspecific PDE inhibitor. In still another group of embodiments the second agent is a superoxide anion ($O_2^-$) scavenger. In yet another group of embodiments the second agent is a β-adrenergic agonist. In another group of embodiments, the second agent is a cAMP-dependent protein kinase activator. In another group of embodiments the second agent is an $\alpha_1$-adrenergic antagonist. In another group of embodiments the second agent is an estrogen, estrogen analog, or estrogenic compound. In another group of embodiments the second agent is an L-type $Ca^{2+}$ channel blocker. In still another group of embodiments the second agent is an ATP-sensitive $K^+$ channel activator. The present invention further provides methods of using the compositions provided above. In a related aspect, the present invention provides compositions comprising a NO donor and a smooth muscle relaxant.

In each of the above embodiments, the nitric oxide donor can be any of a variety of NO donors including, for example, organic NO donors, inorganic NO donors and prodrug forms of NO donors. Preferably, the NO donor includes at least one organic nitrate (including esters of nitric acid) and can be either a cyclic or acyclic compound. For example, suitable NO donors include nitroglycerin (NTG), L-arginine, isosorbide dinitrate (ISDN), isosorbide mononitrate (ISMN) which may include isosorbide-2-mononitrate (IS2MN) and/or isosorbide-5-mononitrate (IS5MN), erythrityl tetranitrate (ETN), pentaerythrityl tetranitrate (PETN), ethylene glycol dinitrate, isopropyl nitrate, glyceryl-1-mononitrate, glyceryl-1,2-dinitrate, glyceryl-1,3-dinitrate, butane-1,2,4-triol trinitrate, and the like. More preferably, the NO donor is NTG. Nitroglycerin and other organic nitrates including ISDN, ETN, and PETN, have been given regulatory approval for use in treatments in other fields of medicine on human subjects. Additional NO donors include sodium nitroprusside, N,O-diacetyl-N-hydroxy-4-chlorobenzenesulfonamide, $N^G$-hydroxy-L-arginine (NOHA), hydroxyguanidine sulfate, molsidomine, 3-morpholinosydnonimine (SIN-1), (±)-S-nitroso-N-acetylpenicillamine (SNAP), S-nitrosoglutathione (GSNO), (±)-(E)-ethyl-2-[(E)-hydroxyimino]-5-nitro-3-hexeneamide (FK409), (±)-N-[(E)-4-ethyl-3-[(Z)-hydroxyimino]-5-nitro-3-hexen-1-yl]-3-pyridinecarboxamide (FR144420), and 4-hydroxymethyl-3-furoxancarboxamide.

In general, the organic nitric oxide donor (e.g., the organic nitrate) is present in any amount less than that which is effective in the practice of the treatment of anal disease when used alone. In typical practice of the invention the organic nitric oxide donor can be present in a concentration from about 0.01 to about 10 percent by weight. All weight percentages herein are based on the total weight of the composition. For NTG, preferred concentrations are in the range of from about 0.01 to about 5 percent by weight.

In one group of embodiments, the composition contains an agent which is a phosphodiesterase (PDE) inhibitor. Inhibitors of phosphodiesterases (PDE), are agents which can block the breakdown of cAMP and cGMP in the tissue. PDE inhibitors include both non-specific PDE inhibitors and specific PDE inhibitors (those which inhibit a single type of phosphodiesterase with little, if any, effect on any other type of phosphodiesterase). Still other useful PDE inhibitors are the dual selective PDE inhibitors (e.g., PDE III/IV inhibitors).

In one group of embodiments, the PDE inhibitor is a PDE V inhibitor. Useful phosphodiesterase type V inhibitors include zaprinast, MBCQ, MY-5445, dipyridamole and sildenifil.

In another group of embodiments, the composition contains an agent which is a phosphodiesterase type II (PDE II) inhibitor. Suitable phosphodiesterase type II inhibitors include EHNA.

In yet another group of embodiments, the composition contains an agent which is a phosphodiesterase type IV (PDE IV) inhibitor. Suitable phosphodiesterase type IV inhibitors include ariflo (SB207499), RP73401, Ro-201724, CDP840, rolipram and LAS31025.

In still another group of embodiments, the composition contains an agent which is a dual selective phosphodiesterase inhibitor, preferably a PDE III/IV inhibitor such as, for example, zardaverine.

In yet another group of embodiments, the composition contains an agent which is a nonspecific phosphodiesterase (nonspecific PDE) inhibitor. Suitable nonspecific phosphodiesterase inhibitors include IBMX, theophylline, dyphylline theobromine, aminophylline, pentoxifylline, papaverine, caffeine and other methyl xanthine and non-xanthine derivatives (Goodman & Gilman's "The Pharmacological Basis of Therapeutics" The McGraw-Hill Companies, 1996).

In still another group of embodiments, the composition contains an agent which is a superoxide anion ($O_2^-$) scavenger. Superoxide can react with NO and dramatically reduce its biological effects. Accordingly, agents that scavenge superoxide anion (e.g., exogenous Mn- or Cu/Zn superoxide dismutase (SOD) or small molecule SOD mimetics, e.g. Mn(III) tetra(4-benzoic acid) porphyrin chloride (MnTBAP) and M40403, see Salvemini, et al., *Science* 286(5438):304–306 (1999)) can enhance the effects of NO. SODs are relatively stable enzymes and can be used in topical formulations with NO donors such as, for example, NTG, to boost the local potency of NO generated from NTG. The nitric oxide formed from NTG acts only locally due to its short half-life. However, NTG itself is stable enough to exert systemic effects following mucosal absorption. By enhancing the local efficacy of NTG with SOD or a SOD mimetic, less NTG is required to produce the same degree of internal anal sphincter relaxation, and less NTG is absorbed, leading to a reduction in systemic side effects.

In yet another group of embodiments, the composition contains an agent which is a β-adrenergic agonist, preferably a $β_2$- or $β_3$-adrenergic receptor agonist. A variety of β-adrenergic agonists have been described in the literature and are useful in the present invention. Suitable $β_3$-adrenergic agonists are described in, for example, Bristol, et al., ANNUAL REPORTS IN MEDICINAL CHEMISTRY, VOL. 33, Chap 19, pp 193–202, Academic Press (1998). Preferred β-adrenergic agonists include salbutamol, terbutaline, procaterol, clenbuterol, isoproterenol, zinterol, BRL 37344, CL316243, CGP-12177A, GS 332, L-757793, L-760087, L-764646, and L-766892.

In another group of embodiments, the agent is a cAMP-dependent protein kinase activator. A variety of cyclic nucleotide-dependent protein kinase activators are useful in the present invention including, for example, cAMP mimetics and dual cGMP/cAMP-dependent protein kinase activators. cAMP mimetics are well known to those of skill in the art and include 8-bromo-cAMP, dibutyryl-cAMP, Rp-cAMPS, and Sp-cAMPS. Dual activators include Sp-8-pCPT-cGMPS, Sp-8-bromo-cGMPS and 8-CPT-cAMP.

In yet another group of embodiments, the composition contains an agent which is an estrogen or estrogen analog or mimetic. As used herein, the term "estrogens" is meant to include all forms of estrogen and estrogen-like compounds such as those compounds having estrogen like activity (e.g., those which bind to the estrogen receptor in a competitive binding assay). The estrogens can be either steroidal or nonsteroidal (see, for example, Bristol, et al., ANNUAL REPORTS IN MEDICINAL CHEMISTRY, VOL. 31, Chap. 19, pp 181–190, Academic Press (1996), and references cited therein). Estrogen-like compounds include but are not limited to 17-beta-estrodiol, estrone, mestranol, estradiol valerate, estrodiol dypionate, ethinyl estrodiol, quinestrol, estrone sulfate, phytoestrogens such as flavones, isoflavones (e.g. genistein), resveratrol, coumestan derivatives, other synthetic estrogenic compounds including pesticides (e.g. p,p'-DDT), plasticizers (e.g. bisphenol A), and a variety of other industrial chemicals (e.g. polychlorinated biphenyls).

In yet another group of embodiments, the composition contains an agent which is an $α_1$-adrenergic antagonist. The sympathetic neurotransmitter norepinephrine contracts sphincter smooth muscle via $α_1$-adrenergic receptors. Pharmacological interference with norepinephrine release or binding to $α_1$-adrenergic receptors by administering sympatholytic agents to the appropriate anal area of a subject can also lead to anal sphincter relaxation, reduction of anal sphincter pressure, maintenance of reduced anal sphincter pressure, and improvement of the signs and symptoms of anorectal disorders. Such sympatholytic agents include $α_1$-adrenergic receptor antagonists (e.g. prazosin, doxazosin, phentolamine, tolazoline, and the like as described in Goodman & Gilman's THE PHARMACOLOGICAL BASIS OF THERAPEUTICS, ninth edition, ed. J G Hardman, et al., McGraw-Hill 1996), $α_2$-adrenergic agonists which block norepinephrine release (e.g. clonidine), nerve terminal norepinephrine depleting agents (e.g. guanethidine, bretylium, reserpine), norepinephrine synthesis inhibitors (e.g. α-methyl tyrosine), and agents which destroy sympathetic nerve terminals (e.g. 6-hydroxy dopamine). Accordingly, in a related embodiment, the composition contains an alternative sympatholytic agent, such as an $α_2$-adrenergic receptor agonist, a nerve terminal norepinephrine depleting agent, a norepinephrine synthesis inhibitor or another agent which destroys sympathetic nerve terminals.

In still another group of embodiments the agent is an ATP-sensitive $K^+$ channel activator. ATP, along with NO, is thought to serve as an inhibitory neurotransmitter released from the enteric non-adrenergic, non-cholinergic nerves that mediate adaptive relaxation of gastrointestinal smooth muscle (Burnstock, *Pharmacol Rev.* 24:509–81 (1972)). ATP appears to act primarily by opening ATP-sensitive potassium ($K_{ATP}$) channels which hyperpolarize the cell membrane, reducing intracellular calcium concentrations, leading to smooth muscle relaxation. Synthetic compounds that activate ATP-sensitive K+ channels are smooth muscle relaxants, e.g. minoxidil, minoxidil sulfate, pinocidil, diazoxide, levcromokalim, cromakalim, etc. (see White, et al., *Eur J Pharmacol.* 357(1):41–51 (1998)). ATP-sensitive potassium channels are expressed in GI smooth muscle (Koh, et al., *Biophys. J.* 75:1793–80 (1998)). Accordingly, specific potassium channel openers will be useful for relaxing internal anal sphincter smooth muscle, reducing anal sphincter pressure, maintaining reduced anal sphincter pressure, and improving the signs and symptoms of anorectal disorders. It should be noted that other $K^+$ channels can also influence smooth muscle tone, including apamin-sensitive low conductance calcium-activated $K^+$ channels and charybdotoxin-sensitive high conductance calcium-activated $K^+$ channels.

In still other embodiments, the compositions will comprise NO donors and smooth muscle relaxants. Preferred smooth muscle relaxants include, for example, hydralazine, papaverine, tiropramide, cyclandelate, isoxsuprine or nylidrin.

In yet other embodiments, the compositions will comprise NO donors and a second agent which is a methyl xanthine or adenosine receptor antagonist. Preferred second agents include theophylline, dyphylline, aminophylline, caffeine, and theobromine.

In a preferred embodiment, a second agent is a $K^+$ATP channel opener, an adenosine receptor antagonist, or a β2-adrenergic receptor agonist. In yet further embodiments, a second agent is preferably selected from the group consisting of theophylline, dyphylline, minoxidil, diazoxide, terbutaline, and salbutamol.

Phosphodiesterase Inhibitor Compositions

In another aspect, the present invention provides compositions for the treatment of anorectal disorders comprising a phosphodiesterase inhibitor, preferably a PDE II inhibitor, a PDE IV inhibitor or a PDE V inhibitor, either alone or in combination with another agent selected from β-adrenergic receptor agonists, $α_1$-adrenergic antagonists, estrogens, L-type $Ca^{2+}$ channel blockers, ATP-sensitive $K^+$ channel activators, or smooth muscle relaxants, in combination with a pharmaceutically acceptable carrier. In other embodiments, the compositions will comprise a dual-selective PDE inhibitor (e.g., a PDE III/IV inhibitor such as zardaverine). The present invention also provides methods of using these compositions.

Phosphodiesterase inhibitors (PDE inhibitors) are agents which can block the breakdown of cAMP and cGMP in the tissue. PDE inhibitors include non-specific PDE inhibitors and specific PDE inhibitors. A non-specific PDE inhibitor inhibits more than one type of phosphodiesterase, while a specific PDE inhibitor inhibits only one type of phosphodiesterase with little, if any, effect on any other type of phosphodiesterase. Specific inhibitors of five cyclic nucleotide PDE isozyme families have been characterized: 8-methoxymethyl-IBMX (isobutyl methylxanthine) or vinpocetine ($Ca^{2+}$, calmodulin-dependent PDE type I); EHNA (erythro-9-(2-hydroxy-3-nonyl)adenine HCl) (cGMP-stimulated PDE type II); milrinone (cGMP-inhibited PDE type III); rolipram (cAMP-specific PDE type IV); and zaprinast and DMPPO (1,3 dimethyl-6-(2-propoxy-5-methane sulphonylamidophenyl)-pyrazolo[3,4-d]pyrimidin-4-(5H)-one) (cGMP-specific PDE type V). Current knowledge suggests that there are at least nine classes of PDE isozymes with type 9A having been recently discovered (see, Fisher, et al., *J Biol. Chem.* 273(25):15559–15564 (1998)). Agents which are non-specific inhibitors of PDEs include, for example, IBMX, theophylline, aminophylline, theobromine, dyphylline caffeine, etc. (see, Vemulapalli, et al., *J Cardiovasc. Pharmacol* 28(6):862–9 (1996)).

Preferably, the compositions for treating anorectal disorders contain one or more compounds selected from the classes of PDE II, PDE IV and PDE V inhibitors, or a dual PDE II/IV inhibitor in a formulation suitable for local treatment. Members of each of these classes can be advantageously combined with a second agent selected from the group of β-adrenergic receptor agonists, preferably a $β_2$- or $β_3$-adrenergic receptor agonists, $α_1$-adrenergic antagonists, L-type $Ca^{2+}$ channel blockers, estrogens, ATP-sensitive $K^+$ channel activators, sympathetic nerve terminal destroyers, adenosine receptor antagonists, methylxanthines, or smooth muscle relaxants. Preferred members from each class of additional agent are those which have been described above for use with NO donors.

In embodiments comprising a second active agent with a PDE, a second agent is preferably a $K^+$ATP channel opener, an adenosine receptor antagonist, or a β2-adrenergic receptor agonist. In yet further embodiments, a preferred second agent is a compound selected from the group consisting of theophylline, dyphylline, minoxidil, diazoxide, terbutaline, and salbutamol.

β-adrenergic Receptor Agonist Compositions

In another aspect, the present invention provides pharmaceutical compositions for the treatment of anorectal disorders comprising a β-adrenergic receptor agonist, preferably a $β_2$- or $β_3$-adrenergic receptor agonist, either alone or in combination with another agent selected from cAMP-hydrolyzing PDE inhibitors (e.g., a PDE IV inhibitor), nonspecific PDE inhibitors, $α_1$-adrenergic antagonists, estrogens, L-type $Ca^{2+}$ channel blockers, ATP-sensitive $K^+$ channel activators, or smooth muscle relaxants, and a pharmaceutically acceptable carrier. The present invention further provides methods of using those compositions.

In this aspect of the invention, the β-adrenergic receptor agonist can be essentially any of the β-adrenergic receptor agonists provided above for use in combination with NO donors. Preferably, the β-adrenergic agonist, is a $β_2$- or $β_3$-adrenergic receptor agonist. Particularly preferred β-adrenergic agonists are those described in Bristol, et al., ANNUAL REPORTS IN MEDICINAL CHEMISTRY, VOL. 33, Chap. 19, pp 193–202, Academic Press (1998) or are selected from salbutamol, terbutaline, procaterol, clenbuterol, isoproterenol, zinterol, BRL 37344, CL316243, CGP-12177A, GS 332, L-757793, L-760087, L-764646, and L-766892.

Terbutaline and salbutamol (albuterol) are β2-adrenergic agonists commonly used for the long-term treatment of obstructive airway diseases and acute bronchospasm in asthma. Beta-adrenergic agents, like VIP, potently relax smooth muscle, including IAS smooth muscle by raising intracellular cyclic AMP levels (Parks et al., *Gut* 10(8): 674–7 (1969); Chakder, S. et al., *Amer J Physiol.* 264 (1 pt 1):G7–12, (1993); Chakder, S. et al., *Amer J Physiol.* 264 (4 pt 1): G702–7, (1993); O'Kelly, T. J. et al., *Gut* 34(5): 689–93, (1993)); O'Kelly, T. J. et al., *Br J Surg* 80(10): 1337–41, (1993)). Cyclic AMP induces smooth muscle relaxation through phosphorylation of smooth muscle regulatory proteins (e.g., myosin light chain kinase) and by decreasing intracellular calcium concentrations (e.g., via $K^+$-ATP channel activation). Terbutaline and salbutamol have weaker cardiovascular effects than non-specific β-receptor agonists, e.g., isoproterenol, because they do not stimulate cardiac $β_1$-adrenergic receptors at therapeutic doses. They are commonly administered by inhalation (i.e., topically). Tolerance is a potential downside effect of $β_2$-adrenergic agonists. Long-term systemic administration of β-adrenergic agonists leads to down-regulation of β receptors in some tissues and decreased pharmacological responses, and has been demonstrated in patients with asthma[1].

[1]Goodman & Gilman's "The Pharmacological Basis of Therapeutics" 9th edition. Chapter 10, Catecholamines, Sympathomimetic Drugs and Adrenergic Receptor Antagonists. Brian B. Hoffman and Robert J. Lefkowitz, 1996.

In one group of embodiments, the compositions comprise forskolin. Forskoline directly activates adenyl cyclase avoiding tolerance.

In one group of embodiments, the composition contains a suitable β-adrenergic receptor agonist and a pharmaceutically acceptable carrier, preferably one formulated for local delivery to the site of the anorectal disease or disorder.

In another group of embodiments, the composition contains another agent selected from cAMP-hydrolyzing PDE inhibitors (e.g., a PDE IV inhibitor), nonspecific PDE inhibitors, $α_1$-adrenergic antagonists, adenosine receptor antagonists including methyl xanthines, estrogens, L-type $Ca^{2+}$ channel blockers, ATP-sensitive $K^+$ channel activators or smooth muscle relaxants.

In one preferred group of embodiments, the agent is a cAMP-hydrolyzing PDE inhibitor, more preferably a phosphodiesterase type IV inhibitor. Preferred phosphodiesterase type IV (also referred to as PDE IV and PDE4) inhibitors are described in, for example, Bristol, et al., Annual Reports in Medicinal Chemistry, Vol. 33, Chap. 10, pp 91–109, Academic Press (1998). Most preferably, the PDE IV inhibitor is rolipram, Ro 20-1724 or Etazolate.

In another group of preferred embodiments, the agent is a nonspecific PDE inhibitor such as, for example, IBMX, aminophylline, theophylline, pentoxifylline, theobromine, dyphylline, lisophylline and papaverine.

In yet another group of preferred embodiments, the agent is an $α_1$-adrenergic antagonist. Suitable $α_1$-adrenergic receptor antagonists (e.g. prazosin, doxazosin, phentolamine, tolazoline, and the like) are described in Goodman & Gilman's THE PHARMACOLOGICAL BASIS OF THERAPEUTICS, ninth edition, ed. J G Hardman, et al., McGraw-Hill (1996). Preferred agents for use in these compositions are selected from prazosin, doxazosin, phentolamine, tolazoline and their derivatives.

In still other preferred embodiments, the adrenergic receptor agonist is combined with an L-type $Ca^{2+}$ channel blocker, such as, for example, nifedipine, nimodipine, felopidine, nicardipine, isradipine, amlodipine, diltiazem, mentol, pinavarium bromide (a gastrointestinal tract selective calcium channel blocker; Awad R A et al., *Acta Gastroent. Latinoamer.* 27:247–251, 1997) and verapamil.

In yet other preferred embodiments, the β-adrenergic receptor agonist is combined with an ATP-sensitive $K^+$ channel activator. Preferred agents within this group are the same as those that have been provided above for use with NO donors.

Additional compositions are those in which a β-adrenergic receptor agonist is combined with an estrogen or estrogen like compound, or with a smooth muscle relaxant. Suitable compounds within each of these classes have been described above for use with NO donors.

In embodiments comprising a second active agent with a $β_2$-adrenergic receptor agonist, a second agent is preferably a $K^+ATP$ channel opener or an adenosine receptor antagonist. In yet further embodiments, a preferred second agent is a compound selected from the group consisting of theophylline, dyphylline, minoxidil, and diazoxide.

Potassium Channel Activator Compositions

In yet another aspect, the present invention provides compositions for the treatment of anorectal disorders comprising an ATP-sensitive $K^+$ channel activator, either alone or in combination with another agent selected from cAMP-dependent protein kinase activators, estrogens, $α_1$-adrenergic antagonists, L-type $Ca^{2+}$ channel blockers, sympathetic nerve terminal destroyers, or smooth muscle relaxants, and a pharmaceutically acceptable carrier. The present invention further provides methods of using those compositions.

In this aspect of the invention, the selected combinations are made from the components described in detail above for the NO donor compositions. Additional description of ATP-sensitive potassium ion channel activators can be found in, for example, Bristol, et al., ANNUAL REPORTS IN MEDICINAL CHEMISTRY, VOL. 29, Chap. 8, pp 73–82, Academic Press (1991). In preferred embodiments the potassium ion channel activator is diazoxide, minoxidil, PCO 400, pinocidil, levcromokalin, or cromokalim.

In some embodiments, the composition comprises an additional agent which is a cAMP-dependent protein kinase activator, an estrogen or estrogen like compound, an $α_1$-adrenergic antagonist, an L-type $Ca^{2+}$ channel blocker, a sympathetic nerve terminal destroyer, or a smooth muscle relaxant. Preferably, the cAMP-dependent protein kinase activator is a cAMP mimetic or a dual cGMP/cAMP-dependent protein kinase activator. More preferably, the cAMP mimetic is 8-bromo-cAMP, dibutyryl-cAMP, Rp-cAMPS, or Sp-cAMPS, and the dual activator is selected from Sp-8-pCPT-cGMPS, Sp-8-bromo-cGMPS and 8-CPT-cAMP.

In one group of embodiments, an $α_1$-adrenergic antagonist is combined with an ATP-sensitive potassium ion channel activator. Preferably, the $α_1$-adrenergic antagonist is prazosin, phentolamine or tolazoline.

In another group of embodiments, an L-type $Ca^{2+}$ channel blocker is combined with an ATP-sensitive potassium ion channel activator. Preferably, the L-type $Ca^{2+}$ channel blocker is nifedipine, nimodipine, felopidine, nicardipine, isradipine, amlodipine, diltiazem, menthol, pinavarium bromide (a gastrointestinal tract selective calcium channel blocker; Awad R A et al., *Acta Gastroent. Latinoamer.* 27:247–251, 1997) or verapamil.

Diazoxide and minoxidil have been used for the treatment of hypertension. These drugs are vasodilators that hyperpolarize arterial smooth muscle cells by activating ATP-sensitive $K^+$ channels (Meisheri et al., *J Pharmacol Exp Ther* 245(3): 751–60 (1988); Standen et al., *Science* 245: 177–80 (1989)). Membrane hyperpolarization inactivates voltage-gated calcium channels, reduces intracellular calcium concentrations, and causes muscle relaxation. ATP released by NANC nerve stimulation probably relaxes the IAS through this mechanism (Brookes *J Gastroenterol Heaptol* 8(6): 590–603 (1993); Rae et al., *J. Physiol* (London) 493 (Pt 2): 517–27 (1996)). Baird and Muir (Baird et al., *Br J Pharmacol* 100(2)329–35 (1990)) demonstrated that cromakalim, a $K^+$-ATP channel opener, inhibited spike discharge, hyperpolarized the membrane and relaxed the guinea pig IAS. In our studies, diazoxide and minoxidil relaxed the rat IAS in vivo. The adverse effects of these drugs are predictable and can be divided into three major categories: 1) fluid and salt retention, 2) cardiovascular effects, and 3) hypertrichosis. Topical minoxidil, inspired by the hypertrichosis side effect, is marketed for stimulating hair growth. This product has an excellent safety record and is now sold over the counter.

In still another group of embodiments, a smooth muscle relaxant is combined with an ATP-sensitive potassium ion channel activator. Preferably, the smooth muscle relaxant is hydralazine, papaverine, tiropramide, cyclandelate, isoxsuprine or nylidrin.

In embodiments comprising a second active agent with a $K^+ATP$ channel opener, a second agent is preferably a $K^+ATP$ channel opener, a $β_2$-adrenergic receptor agonist, or an adenosine receptor antagonist. In yet further embodiments, a preferred second agent is a compound selected from the group consisting of theophylline, dyphylline, terbutaline, and salbutamol.

$α_1$-Adrenergic Antagonist Compositions

In still another aspect, the present invention provides compositions for the treatment of anorectal disorders comprising an $α_1$-adrenergic antagonist, either alone or in combination with another agent selected from cAMP-hydrolyzing PDE inhibitors (preferably a PDE IV inhibitor), estrogens, sympathetic nerve terminal destroyers, or smooth muscle relaxants, and a pharmaceutically acceptable carrier. The present invention further provides methods of using those compositions.

$α_1$-Adrenergic antagonists which are useful in this aspect of the invention have been described above and can be found in, for example, Goodman & Gilman's THE PHARMACOLOGICAL BASIS OF THERAPEUTICS, ninth edition, ed. J G Hardman, et al., McGraw-Hill (1996). Preferred $α_1$-adrenergic antagonists are prazosin, phentolamine and tolazoline.

For those embodiments in which an $α_1$-adrenergic antagonist is combined with a cAMP-hydrolyzing PDE inhibitor (preferably a PDE IV inhibitor), an estrogen or estrogen like compound, a sympathetic nerve terminal destroyer, or a smooth muscle relaxant, the preferred members of each class are those which have been described above for use with NO donors.

In embodiments comprising a second active agent with a $α_1$-adrenergic antagonist, a second agent is preferably a $K^+ATP$ channel opener, a $β_2$-adrenergic receptor agonist or an adenosine receptor antagonist. In yet further embodiments, a preferred second agent is a compound selected from the group consisting of theophylline, dyphylline, minoxidil, diazoxide, terbutaline, and salbutamol.

Cyclic Nucleotide-Dependent Protein Kinase Activator Compositions

In another aspect, the present invention provides pharmaceutical compositions for the treatment of anorectal disorders comprising cyclic nucleotide-dependent protein kinase activators, either alone or in combination with another agent. Methods for the use of these compositions are also provided. In one group of embodiments, cGMP-dependent protein kinase activators are used alone. In another group of embodiments, nonspecific cyclic nucleotide-dependent protein kinase activators are used alone. In yet another group of embodiments, nonspecific cyclic nucleotide-dependent protein kinase activators are used in combination with smooth muscle relaxants. In still another group of embodiments, cAMP-dependent protein kinase activators are provided in combination with L-type $Ca^{2+}$ channel blockers.

In embodiments comprising a second active agent with the protein kinase activator, a second agent is preferably a $K^+$ATP channel opener, $\beta_2$-adrenergic receptor agonist or an adenosine receptor antagonist. In yet further embodiments, a preferred second agent is a compound selected from the group consisting of theophylline, dyphylline, terbutaline, minoxidil, diazoxide and salbutamol.

In each instance, preferred members of the recited classes of compounds are those that have been described above for use alone or in other combinations.

Estrogen and Estrogen Mimetic Compositions

In another aspect, the present invention provides pharmaceutical compositions for the treatment of anorectal disorders comprising estrogen or an estrogen mimetic, either alone or in combination with another agent from any of the classes of agents described above. Estrogen-like compounds include but are not limited to 17-beta-estrodiol, estrone, mestranol, estradiol valerate, estrodiol dypionate, ethinyl estrodil, quinestrol, estrone sulfate, phytoestrogens such as flavones, isoflavones (e.g. genistein), resveratrol, coumestan derivatives, other synthetic estrogenic compounds including pesticides (e.g. p,p'-DDT), plasticizers (e.g. bisphenol A), and a variety of other industrial chemicals (e.g. polychlorinated biphenyls) (Goodman & Gilman's THE PHARMACOLOGICAL BASIS OF THERAPEUTICS, ninth edition, ed. J G Hardman, et al., McGraw-Hill (1996). Preferred agents are selected from those described with reference to the compositions of single agents or combinations above. Methods for the use of these compositions are also provided.

In embodiments comprising a second active agent with the estrogenic agent, a second agent is preferably a $K^+$ATP channel opener, a $\beta_2$-adrenergic receptor agonist or an adenosine receptor antagonist. In yet further embodiments, a preferred second agent is a compound selected from the group consisting of theophylline, dyphylline, terbutaline, minoxidil, diazoxide and salbutamol.

Sympathetic Nerve Terminal Destroyer Compositions

In another aspect, the present invention provides pharmaceutical compositions for the treatment of anorectal disorders comprising a sympathetic nerve terminal destroyer, either alone or in combination with another agent from any of the classes of agents described above. The sympathetic nerve terminal destroyer compounds include but are not limited to 6-hydroxydopamine and its analogs See, Goodman & Gilman's THE PHARMACOLOGICAL BASIS OF THERAPEUTICS, ninth edition, ed. J G Hardman, et al., McGraw-Hill (1996). Preferred agents are selected from those described with reference to the compositions of single agents or combinations above. Methods for the use of these compositions are also provided.

Adenosine Receptor Antagonists/Methylxanthines

In another aspect, the present invention provides pharmaceutical compositions for the treatment of anorectal disorders comprising a adenosine receptor antagonist, either alone or in combination with another agent from any of the classes of agents described above. Examples of adenosine receptor antagonists include theophylline and dyphylline. See, Goodman & Gilman's THE PHARMACOLOGICAL BASIS OF THERAPEUTICS, ninth edition, ed. J G Hardman, et al., McGraw-Hill (1996). Preferred agents are selected from those described with reference to the compositions of single agents or combinations above. Methods for the use of these compositions are also provided.

Theophylline, a plant-derived methylxanthine, has been used for the treatment of bronchial asthma for decades. Theophylline relaxes smooth muscle, notably bronchial muscle, that has been contracted experimentally with a spasmogen, or clinically in asthma. We found that theophylline relaxed the rat IAS when instilled into the distal anal canal. Proposed mechanisms of methylxanthine-induced physiologic and pharmacological effects include: 1) inhibition of phosphodiesterases, thereby increasing intracellular cyclic AMP, 2) direct effects on intracellular calcium concentration, 3) indirect effects on intracellular calcium concentrations via cell membrane hyperpolarization, 4) uncoupling of intracellular calcium increases with muscle contractile elements, and 5) antagonism of adenosine receptors. Adenosine receptor antagonism is thought to be the most important factor responsible for most of the pharmacological effects of methylxanthines in therapeutically administered doses[2].

[2] Goodman & Gilman's "The Pharmacological Basis of Therapeutics" 9th edition. Chapter 28, Drugs Used in the Treatment of Asthma. William E. Serafin, 1996.

We have found the related compound, dyphylline, to also reduce IASP in tests. Dyphylline is not metabolized by the liver and is excreted unchanged by the kidneys, therefore its pharmacokinetics and plasma levels are independent of factors that effect liver enzymes such as smoking, age, congestive heart failure, or the use of other drugs that affect liver function.

In embodiments comprising a second active agent with the adenosine receptor antagonist, a second agent is preferably a $K^+$ATP channel opener or a $\beta_2$-adrenergic receptor agonist. In yet further embodiments, a preferred second agent is a compound selected from the group consisting of terbutaline, minoxidil, diazoxide and salbutamol.

Formulations for the Treatment of Anorectal Disorders

Many of the individual components of the compositions above have been described for use in a variety of disease states. However, certain classes and combinations of classes have now been found to be useful for the treatment of anorectal diseases and can be provided in formulations best suited for delivery to an appropriate anal area. Preferred formulations are those in which the components are combined in a topical formulation for local application to the external or internal anus, the external or internal anal sphincter, anal sphincter muscle, the external or internal anal canal and the lower rectum above the anal canal.

Accordingly, each of the compositions provided above will typically be presented in an appropriate pharmaceutical formulation comprising an effective amount of the noted agents (e.g., NO donors, $\beta_2$- or $\beta_3$-adrenergic receptor agonists, cAMP-hydrolyzing PDE inhibitors, nonspecific PDE inhibitors, $\alpha_1$-adrenergic antagonists, L-type $Ca^{2+}$ channel blockers, ATP-sensitive $K^+$ channel activators, adenosine receptor antagonists, and the like).

One of skill in the art will appreciate that suitable formulations are dependent on the form of delivery to be employed, and all such forms are contemplated by the present invention. Additionally, in some embodiments, combinations of agents are employed in a single formulation, while in other embodiments, agents are formulated separately, but administered in combination, or sequentially. In the discussion below, compositions of single agents will be understood to also include compositions of two or more agents. Still further, different formulations can be used for those embodiments in which agents are administered separately or sequentially, by different routes of administration.

Topical Compositions

In view of the above, the present invention provides topical compositions useful for treating anorectal disorders (including those related to hypertonicity and/or spasm of the internal anal sphincter muscle, e.g. hemorrhoidal pain) and for treating spasms of the mammal, including humans, which comprise an effective amount of an agent that reduces the contraction of anal sphincter muscle or maintains a reduced contraction of the anal sphincter muscle, and a pharmaceutically acceptable carrier. In one embodiment, the agent is an ATP-sensitive potassium channel opener. In another embodiment, the agent is a phosphodiesterase inhibitor, a cyclic nucleotide mimic, β-adrenergic agonist, an estrogen or estrogen like compound, an $\alpha_1$-adrenergic antagonist or a potassium channel opener.

In related embodiments, the present invention provides topical pharmaceutical compositions in unit dosage form comprising per unit dosage an amount of the agent or combination provided above, which is effective for treating an anal disorder in a subject in need of such treatment. Typically the agents are in combination with a pharmaceutically acceptable carrier. Such compositions are useful in treating or reducing pain associated with anal disorders, such as hemorrhoidal pain, and for treating spasms and/or hypertonicity of the sphincters, including the internal anal sphincter, lower esophageal sphincter, pyloric sphincter, sphincter of Oddi, and the ileocolic sphincter. The topical composition is also useful in treating conditions resulting from spasms and/or hypertonicity of sphincters of the anorectal region including anal fissure, post-operative rectal pain, hypertrophic pyloric stenosis, and pancreatitis, as well as conditions resulting from general spasm of the muscles of the GI tract including Zenkers diverticulum, achalasia, esophageal spasm (nutcracker esophagus), irritable bowel disease, and Hirshprungs disease (bowel obstruction). In addition, the topical compositions are useful for relaxing the anal sphincter, reducing anal sphincter pressure or maintaining reduced anal sphincter pressure and reducing pain and discomfort before, during and after examinations of the anus, rectum and lower gastrointestinal system, insertion of instruments, and procedures such as colonoscopy, cystoscopy and surgery.

Dosage Forms

Topical Administration

Dosage forms for the topical administration of the anal sphincter relaxing agents of this invention include powders, sprays, ointments, pastes, creams, lotions, gels, solutions, patches, suppositories and liposomal preparations. The dosage forms may be formulated with mucoadhesive polymers for sustained release of the active compound(s) at the anal mucosa. The active compound may be mixed under sterile conditions with a pharmaceutically acceptable carrier, and with any preservatives, buffers, or propellants, which may be required. Topical preparations can be prepared by combining the anal sphincter relaxing agent with conventional pharmaceutical diluents and carriers commonly used in topical dry, liquid, cream and aerosol formulations. Ointment and creams may, for example, be formulated with an aqueous or oily base with the addition of suitable thickening and/or gelling agents. Such bases may include water and/or an oil such as liquid paraffin or a vegetable oil such as peanut oil or castor oil. Thickening agents which may be used according to the nature of the base include soft paraffin, aluminum stearate, cetostearyl alcohol, propylene glycol, polyethylene glycols, woolfat, hydrogenated lanolin, beeswax, and the like. Lotions may be formulated with an aqueous or oily base and, in general, also include one or more of the following: stabilizing agents, emulsifying agents, dispersing agents, suspending agents, thickening agents, coloring agents, perfumes, and the like. Powders may be formed with the aid of any suitable powder base, e.g., talc, lactose, starch, and the like. Drops may be formulated with an aqueous base or non-aqueous base also comprising one or more dispersing agents, suspending agents, solubilizing agents, and the like.

The ointments, pastes, creams and gels also may contain excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays also can contain excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Representative compositions include topical compositions comprising one or more of the following first pharmacologic agents: an NO donor, phosphodiesterase inhibitor, cyclic nucleotide mimetic, β-adrenergic agonist, L-type calcium channel blocker, α-adrenergic antagonist, ATP-sensitive potassium channel activator, sympathetic nerve terminal destroyer, estrogen or estrogen-like compound or botulinum toxin in combination with a pharmaceutically acceptable carrier and at least one of the following second pharmacologic agents: a local anesthetic (e.g., lidocaine, prilocaine, etc.), local anti-inflammatory agent (e.g., naproxen, pramoxicam, etc.), corticosteroid (e.g., cortisone, hydrocortisone, etc.), anti-itch agent (e.g., loperamide diphylenoxalate, etc.), an agent that interferes with the activation of peripheral sensory neurons, including divalent and trivalent metal ions (e.g., manganese, calcium, strontium, nickel, lanthanum, cerium, zinc, etc.), analgesic agents, yeast-based product (e.g., lyophilized yeast, yeast extract, etc.), growth-promoting and/or wound healing-promoting agent known to promote re-epithelialization (e.g., platelet-derived growth factor PDGF, interleukin-11 (IL-11) etc.), anti-microbial agent (e.g., neosporin, polymyxin B sulfate, bacitracin zinc, etc.), mucoadhesive agent (e.g., cellulose derivatives, etc.), cytoprotectant agent (e.g., colloidal bismuth, misoprostol, etc., with the exception of sucralfate) as defined in GOODMAN & GILMAN'S THE PHARMACOLOGICAL BASIS OF THERAPEUTICS, supra, an agent that promotes local tissue sclerosis (e.g., alum, etc.), or menthol. The first pharmacologic agent is typically present in the composition in unit dosage form effective for treatment of a first medical condition(s), such as an anal disease or pain associated with an anal disease. The second pharmacologic agent is typically present in the composition in unit dosage form effective for treatment of a second medical condition(s), or a condition(s), symptom(s) or effect(s) associated with or resulting from the first medical condition(s).

In one aspect, the invention provides compositions for treating anorectal disorders which comprise an active agent and a pharmaceutically acceptable carrier. The active agent comprises an agent that stimulates or causes an increase of either cGMP or cAMP through activation of guanylyl or adenylyl cyclase, respectively, a cyclic nucleotide mimetic, PDE inhibitor, α-adrenergic receptor antagonist, or β-adrenergic receptor agonist, or potassium channel opener. In one aspect, the active agent is present in compositions of the invention in an amount of from about 0.001% to about 15% by weight of the composition. In another aspect, the active agent is present in an amount of from about 0.01% to about 7.5% by weight, more preferably from about 0.05% to about 2% by weight of the composition.

For example, in one group of embodiments, the invention provides compositions for treating anorectal disorders comprising a pharmaceutically acceptable carrier and an amount of from about 0.001% to about 15% sildenafil by weight. In another aspect, compositions comprising a pharmaceutically acceptable carrier and an amount of from about 0.01% to about 7.5% or from about 0.05% to about 2% sildenafil by weight are provided.

The topical pharmaceutical compositions can also include one or more preservatives or bacteriostatic agents, e.g., methyl hydroxybenzoate, propyl hydroxybenzoate, chlorocresol, benzalkonium chlorides, and the like. The topical pharmaceutical compositions also can contain other active ingredients such as antimicrobial agents, particularly antibiotics, anesthetics, analgesics, and antipruritic agents.

One example of a topical formulation includes 75% (w/w) white petrolatum USP, 4% (w/w) paraffin wax USP/NF, lanolin 14% (w/w), 2% sorbitan sesquioleate NF, 4% propylene glycol USP, and 1% anal sphincter relaxing agent.

The dosage of a specific anal sphincter relaxing agent depends upon many factors that are well known to those skilled in the art, for example, the particular agent; the condition being treated; the age, weight, and clinical condition of the recipient patient; and the experience and judgment of the clinician or practitioner administering the therapy. An effective amount of the compound is that which provides either subjective relief of symptoms or an objectively identifiable improvement as noted by the clinician or other qualified observer. The dosing range varies with the compound used, the route of administration and the potency of the particular compound.

Transmucosal (i.e., sublingual, rectal, colonic, pulmonary, buccal and vaginal) drug delivery provides for an efficient entry of active substances to systemic circulation and reduces immediate metabolism by the liver and intestinal wall flora (See Chien Y. W., NOVEL DRUG DELIVERY SYSTEMS, Chapter 4 "Mucosal Drug Delivery," Marcel Dekker, Inc. (1992). Transmucosal drug dosage forms (e.g., tablet, suppository, ointment, gel, pessary, membrane, and powder) are typically held in contact with the mucosal membrane and disintegrate and/or dissolve rapidly to allow immediate local and systemic absorption. These formulations are used along with the anti-inflammatory agents of the present invention for reducing or eliminating inflammation of transmucosal membranes.

In order to enhance transmucosal absorption efficiency and bioavailability of the active agents, selected mucosal adhesive polymers or dosages can be employed. For example, a selected potassium channel opener, e.g. minoxidil can be formulated in a liquid suppository in which mucoadhesive polymers such as polyvinylpyrrolidone (PVP, BASF, Germany), polycarbophil (Goodrich, USA), or sodium alginate (Hayashi Pure Chemicals, Tokyo, Japan), etc. are incorporated. This type of liquid suppository has a gelation temperature between 30 to 36° C. and has a mucoadhesive force of 430 to 5800 dyne/cm. As a result, the suppository remains as an easy to apply liquid at room temperature, gels at physiological temperature and remain adhered to the anal mucosal membrane for a sustained period of time (Rye J M et al., *Journal of Controlled Release*, 59:163–172. 1999; *Chem Pharm Bull*, 46 (2):309–313, 1998; *J Pharm Sci*, 81(11):1119–1125, 1992; *Chem Pharm Bull*, 37(3):766–770, 1989; *J Pharmacobiodyn*, 9(6):526–531,1986; *J Pharm Sci.* 84(1):15–20, 1995).

Preferred formulations are either as solutions or semi-solid preparations (gel, ointment, suspension, lotion, cream, etc.). Suitable excipients, depending on the agent, include petrolatum, lanolin, methylcellulose, sodium carboxymethylcellulose, hydroxpropylcellulose, sodium alginate, carbomers, glycerin, glycols, oils, glycerol, benzoates, parabens and surfactants. It will be apparent to those of skill in the art that the solubility of a particular compound will, in part, determine how the compound is formulated. An aqueous gel formulation will is suitable for soluble compounds. Where a compound is insoluble at the concentrations required for activity, a cream or ointment preparation will typically be preferable. In this case, oil phase, aqueous/organic phase and surfactant may be required to prepare the formulations. Thus, based on the solubility and excipient-active interaction information, the dosage forms can be designed and excipients can be chosen to formulate the prototype preparations. Particularly preferred preparations include those in a suppository or sustained release format.

Sustained or Controlled Delivery Formulations

In yet other embodiments, the invention provides topical sustained and prolonged release pharmaceutical compositions comprising one or more anal sphincter relaxant, including nitric oxide donors (such as nitroglycerin, isosorbide dinitrate, and L-arginine) or the pharmacological agents described above and a pharmaceutically acceptable carrier, to treat anorectal disorders. The compositions are useful in the treatment of such disorders as reducing anal sphincter pressure, maintaining reduced anal sphincter pressure, and in controlling and reducing pain associated with such disorders. Such compositions may comprise a unit dosage of one or more active agents (e.g., nitric oxide donor) which is effective in treating anal disorders and in controlling and alleviating pain associated therewith. Preferably, the compositions are administered in unit dosage form to a subject in need of such treatment. In other embodiments, the compositions contain an NO donor in an amount which is less than an effective amount when used alone, but which is effective when used in combination with a second agent which modulates levels of cAMP or cGMP in a subject. Topical sustained and prolonged release compositions are typically variants which include 1) an absorbent in a hydrophilic base; 2) an absorbent in a hydrophobic base; and 3) coated beads containing an absorbent matrix dispersed in a suitable vehicle. Also provided are methods of treating anal or GI tract disorders comprising topically administering an effective amount of such compositions (e.g., in unit dosage form) to the appropriate anal area of the subject in need of such treatment.

Such hydrophilic compositions and preparations of the invention comprise a nitric oxide donor (or other suitable agent or combination of agents) and a polymer, such as cellulose (methyl cellulose, ethyl cellulose, hydroxy propyl cellulose, etc.), higher molecular weight polyethylene glycol, methacrylic-acrylic acid emulsion, hydrogel, carbopol, ethyl vinyl acetate copolymer, or polyester, etc., to bind the nitric oxide donor to the polymer. The nitric oxide donor-polymer matrix or agent-polymer matrix is then dispersed in a hydrophilic vehicle to form a semi-solid. After administration of such hydrophilic composition into the appropriate anal area, such as the anal canal or anal sphincter, the water in the semi-solid preparation is adsorbed and the polymer matrix with the active ingredient—the nitric oxide donor or other agent—remains as a coating in the anal region or area to which it has been applied. The nitric oxide donor is then slowly released from this coating.

Hydrophobic compositions and preparations of the inventions employ similar polymers as used in the hydrophilic preparations, but the polymer/nitric oxide donor matrix is dispersed into a vehicle, such a plastibase, in the hydrophobic compositions and preparations. Plastibase is a mineral oil base that only partially dissolves the nitric oxide donor. The semi-solid composition forms a thin coating on the anal region to which the composition has been applied (such as the anal canal or anal sphincter area) and slowly releases the active. The prolonged action is controlled principally by the solubility of the active ingredient (nitric oxide donor) in the vehicle.

The present invention also provides coated beads which are produced by first absorbing the nitric oxide donor or other agent or combination of agents on a cellulosic material blended with polyethylene glycol, filler, binder and other excipients. The resulting matrix is then extruded and spheronized (e.g., the process of making into spheres) to create small beads. The beads are then coated to an appropriate thickness with one or more of a suitable material, such as a methacrylic-acrylic polymer, polyurethane, ethyl vinyl acetate copolymer, polyester, silastic, etc. The coating on the beads acts as a rate controlling membrane which regulates the release of the agent from the core beads.

Oral Formulations

In still another embodiment, the invention provides pharmaceutical compositions suitable for oral administration which are provided in unit dosage form comprising per unit dosage a phosphodiesterase inhibitor, cyclic nucleotide mimetic, or β-adrenergic agonist, and a pharmaceutically acceptable carrier. Such compositions are useful for treating anorectal disorders, including those disorders and conditions provided above.

For delivery to the buccal membranes, typically an oral formulation, such as a lozenge, tablet, or capsule is used. The method of manufacture of these formulations are known in the art, including but not limited to, the addition of a pharmacological agent to a pre-manufactured tablet; cold compression of an inert filler, a binder, and either a pharmacological agent or a substance containing the agent (as described in U.S. Pat. No. 4,806,356); and encapsulation. Another oral formulation is one that can be applied with an adhesive, such as the cellulose derivative, hydroxypropyl cellulose, to the oral mucosa, for example as described in U.S. Pat. No. 4,940,587. This buccal adhesive formulation, when applied to the buccal mucosa, allows for controlled release of the pharmacological agent into the mouth and through the buccal mucosa. The anti-inflammatory agents of the present invention can be incorporated into these formulations as well.

Aerosol Formulations

For delivery to the nasal or bronchial membranes, typically an aerosol formulation is employed. The term "aerosol" includes any gas-borne suspended phase of the pharmacological agent which is capable of being inhaled into the bronchioles or nasal passages. Specifically, aerosol includes a gas-borne suspension of droplets of the compounds of the instant invention, as may be produced in a metered dose inhaler or nebulizer, or in a mist sprayer. Aerosol also includes a dry powder composition of a compound of the pharmacological agent suspended in air or other carrier gas, which may be delivered by insufflation from an inhaler device, for example. For solutions used in making aerosols, the preferred range of concentration of the pharmacological agent is 0.1–100 milligrams (mg)/milliliter (mL), more preferably 0.1–30 mg/mL, and most preferably, 1–10 mg/mL. Usually the solutions are buffered with a physiologically compatible buffer such as phosphate or bicarbonate. The usual pH range is 5 to 9, preferably 6.5 to 7.8, and more preferably 7.0 to 7.6. Typically, sodium chloride is added to adjust the osmolarity to the physiological range, preferably within 10% of isotonic. Formulation of such solutions for creating aerosol inhalants is discussed in Remington's Pharmaceutical Sciences, see also, Ganderton and Jones, DRUG DELIVERY TO THE RESPIRATORY TRACT, Ellis Horwood (1987); Gonda (1990) *Critical Reviews in Therapeutic Drug Carrier Systems* 6:273–313; and Raeburn et al., (1992) *J Pharmacol Toxicol Methods* 27:143–159.

Solutions of the pharmacological agent may be converted into aerosols by any of the known means routinely used for making aerosol inhalant pharmaceuticals. In general, such methods comprise pressurizing or providing a means of pressurizing a container of the solution, usually with an inert carrier gas, and passing the pressurized gas through a small orifice, thereby pulling droplets of the solution into the mouth and trachea of the animal to which the drug is to be administered. Typically, a mouthpiece is fitted to the outlet of the orifice to facilitate delivery into the mouth and trachea.

Parenteral Formulations

In yet another embodiment, the invention provides pharmaceutical compositions suitable for parental administration which are provided in unit dosage form comprising per unit dosage a phosphodiesterase inhibitor, cyclic nucleotide mimetic, or β-adrenergic agonist, and a pharmaceutically acceptable carrier. Such compositions are useful for treating anorectal disorders and conditions as described above.

Methods of Treating Anorectal Disorders

In another aspect, the present invention provides methods for treating anorectal disorders which comprise administering to an appropriate anal area or affected anal tissue (e.g., external or internal anal tissue or anal canal) of a subject in need of such treatment an effective amount of any of the compositions provided above. By use of such methods of the invention, anorectal hypertonicity and/or spasms are relieved, anal sphincter pressure is reduced, reduced anal sphincter pressure is maintained, and signs and symptoms associated with anorectal disorders, e.g. anal fissures, anal ulcers and hemorrhoids, and pain are improved. The methods described herein are also applicable to the treatment of recurrent anal diseases, and are also useful for relaxing the anal sphincter and reducing pain during anorectal exams (in patients with and without disorders), particularly during procedures when instruments are inserted into the anus.

The present invention further provides methods of using the compositions above in combination with local anesthetic agents, for example lidocaine, prilocaine, etc. Each of the compositions will typically be in a pharmaceutically acceptable dosage form as an effective treatment for a medical condition such as hemorrhoidal pain and for treating spasms and/or hypertonicity of the sphincters including the internal anal sphincter, lower esophageal sphincter, pyloric sphincter, sphincter of Oddi, and the ileocolic sphincter. These pharmaceutical preparations are also useful in treating conditions resulting from spasms and/or hypertonicity of sphincters of the anorectal region including anal fissure, post-operative rectal pain, hypertrophic pyloric stenosis, and pancreatitis, as well as conditions resulting from general spasm of the muscles of the GI tract including Zenkers diverticulum, achalasia, esophageal spasm (nutcracker esophagus), irritable bowel disease, and Hirschsprung's disease (bowel obstruction). In another aspect, the present invention provides methods for treating anal disorders which comprise administering an effective amount of such composition along with a local anesthetic agent to a subject in need of such treatment. Such compositions can be administered orally, topically, or parenterally.

Similarly, the invention provides methods of using the compositions above in combinations with local anti-inflammatory agents, for example, naproxen, piroxicam, etc. in a pharmaceutically acceptable dosage form as an effective treatment for a medical condition such as hemorrhoidal pain and for treating hypertonicity and/or spasms of the sphincters including the internal anal sphincter, lower esophageal sphincter, pyloric sphincter, sphincter of Oddi, and the ileocolic sphincter. These pharmaceutical preparations are also useful in treating conditions resulting from spasms and/or hypertonicity of sphincters of the anorectal region including anal fissure, post-operative rectal pain, hypertrophic pyloric stenosis, and pancreatitis, as well as conditions resulting from general spasm of the muscles of the GI tract including Zenkers diverticulum, achalasia, esophageal spasm (nutcracker esophagus), irritable bowel disease, and Hirschsprung's disease (bowel obstruction). In another aspect, the present invention provides methods for treating anal disorders which comprise administering an effective amount of such composition along with a local anesthetic agent to a subject in need of such treatment. Such compositions can be administered orally, topically, or parenterally.

Additional methods provided by the present invention are those in which two or more agents selected from NO donors, phosphodiesterase type V (PDE V) inhibitor, a phosphodiesterase type II (PDE II) inhibitor, a nonspecific PDE inhibitor, a dual-selective PDE inhibitor, a β-adrenergic agonist, a cAMP-dependent protein kinase activator, an $\alpha_1$-adrenergic antagonist, a superoxide anion ($O_2^-$) scavenger, an ATP-sensitive $K^+$ channel activator, an estrogen or estrogen mimetic, a sympathetic nerve terminal destroyer, an adenosine receptor antagonist, or a smooth muscle relaxant, are administered either in combination or sequentially to provide an enhanced therapeutic benefit. In particular, the use of an NO donor and a second agent from those provided above can provide fewer and less severe side effects than equally effective doses of NO donors, if used alone. More particularly, the use of an NO donor in combination with a second agent allows for decreased amounts of the NO donor to be used to achieve the same benefit relative to use alone, while extending the period of reduction of anal sphincter pressure, and provides significantly reduced occurrence and duration of headaches.

EXAMPLES

Example 1

This example illustrates the effect of cGMP mimetics, alone and in combination with a NO donor in a rat internal anal sphincter (IAS) relaxation model.

Male Sprague-Dawley rats (300–400 gm) were anesthetized with ketamine (90 mg/kg), xylazine (9 mg/kg) given intramuscularly and supplemented as needed with $\frac{1}{3}^{rd}$ dose. Rats were gently restrained on their backs on a heated surgical table (Harvard Apparatus) for the duration of the experiments. The diuretic effects of anesthesia was offset by rehydration with saline through an intraperitoneal implanted 24 gauge angiocatheter (VWR, San Francisco, Calif.). The constriction/relaxation measurement assembly included a Millar catheter/transducer (1.67 mm diameter.) connected to a Digi-Med Low Pressure Analyzer (Micro-Med) accurate for pressure measurements between –50 and 150 mmHg. The data were integrated and converted to waveforms with the Digi-Med System Integrator software. Blood pressure changes were monitored using an arterial catheter/transducer and a Digi-Med Blood Pressure Analyzer with the DMSI software. Respiratory changes were monitored using a mercury strain gauge/transducer, wrapped around the rib-cage of the rat, hooked up to a Digi-Med Analog Signal Analyzer along with the DMSI software. Drug delivery was accomplished through two Hamilton syringes with no dead space using PE 10 tubing adjacent to the catheter sensor. Drugs, typically were applied soon after stable baseline readings are recorded. Although unanesthetized restrained rats had been used in other studies, no differences have been observed in resting anal pressures after anesthesia; therefore, these studies were carried out with anesthetized rats to avoid undue distress to the animals.

Figure 2:
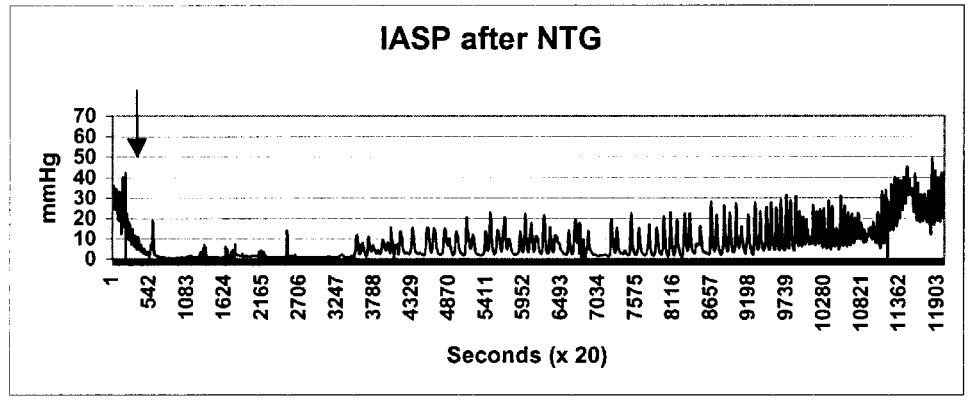
FIG. 2 illustrates the waveform pattern for IASP in a rat following administration of 20 μl of a 1% solution of nitroglycerin in propylene glycol.

Typical resting mean internal anal sphincter pressures (IASP) varied between 30 and 60 mmHg in this model. The Millar catheter sensor allowed for accurate, isolated recordings of the IAS. FIG. 1 represents a typical waveform pattern for resting IASP in a rat under conditions of a control experiment. The first 10 minutes after treatment with nitroglycerin is shown in FIG. 2.

Figure 3:
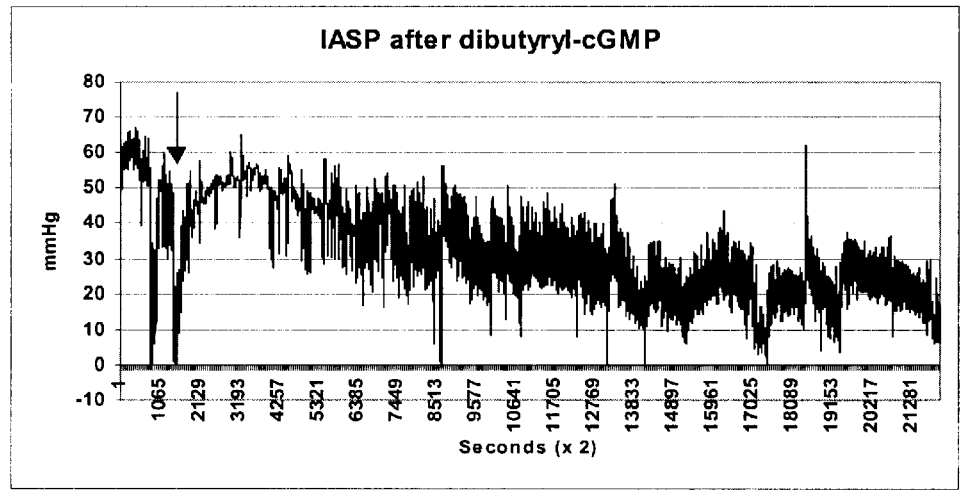
FIG. 3 illustrates the effect of a cGMP mimetic on internal anal sphincter pressure in a rat. The figure shows a waveform pattern for IASP for a rat following administration of 20 μl of a 10% solution of dibutyryl-cGMP in saline.

Using the same experimental protocol, the effect of a cGMP mimetic, dibutyryl-cGMP was studied. FIG. 3 shows that 20 µl of a 10% solution of dibutyryl-cGMP in saline applied to the anal canal reduced the mean IASP by 45% over 2.5 hours following treatment. The average IASP over the last hour prior to terminating the experiment had dropped 60%.

The IASP was still reduced 34% by the following morning indicating a potential long-term effect of the drug. A subsequent dose of 1% nitroglycerin dropped the IASP by 24% for 30 minutes and 71% for the first 10 minutes following treatment. After IASP returned to pre-treatment levels, a further dose of dibutyryl-cGMP was administered and found to lower IASP 15% over the ensuing 3 hours and 10 minutes.

These results support the effect of cGMP mimetics in relaxing anal sphincter muscle tone, and more importantly, suggest a potential benefit of using a combination of NO donor and cGMP mimetic due the quick onset of action of the NO donor and the more prolonged duration of relaxation produced by the cGMP mimetics.

Example 2

This example illustrates the effect of phosphodiesterase inhibitors in a rat internal anal sphincter relaxation model.

Figure 4:
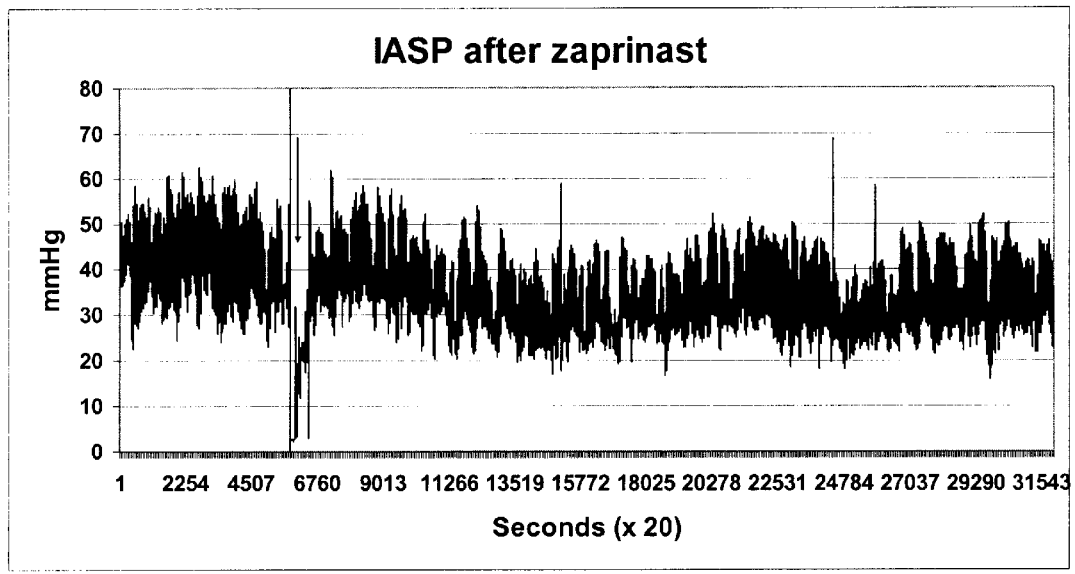
FIG. 4 illustrates the effect of a type V phosphodiesterase inhibitor on internal anal sphincter pressure in a rat. The figure shows a waveform pattern for IASP for a rat following administration of 20 μl of a 5% solution of zaprinast in 1-methyl-2-pyrrolidinone.

Using the same experimental protocol described above, an application of 20 µL of a 5% zaprinast solution in 1-methyl-2-pyrrolidinone reduced mean IASP by 21% over 32 minutes compared with vehicle treatment alone. The effect of phosphodiesterase inhibitors could be further enhanced by minimal concentrations of NO donors, such as nitroglycerin that produced a quicker onset and sustained sphincter relaxation without headache and other adverse reactions observed with high dose of NO donors alone (see FIG. 4).

Example 3

This example illustrates the effect of a potassium channel opener (minoxidil) in a rat internal anal sphincter constriction/relaxation model.

Figure 5:
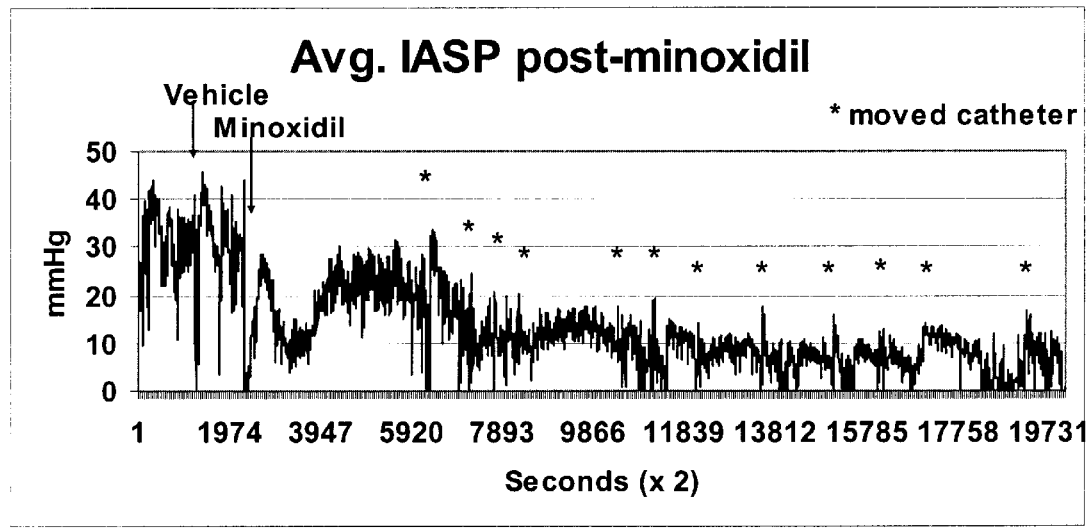
FIG. 5 illustrates the effect of a potassium channel opener on internal anal sphincter pressure in a rat. The figure shows a waveform pattern for IASP for a rat following administration of 20 μl of a 4% solution of minoxidil in 62.5% propylene glycol.

Following the same experimental protocol as described above, a single 20 μl dose of a 4% solution of minoxidil in 62.5% propylene glycol resulted in a 64% reduction of the IASP over 2.5 hours following treatment. The vehicle alone had little effect on IASP (see FIG. 5).

Example 4

This example illustrates the use of a variety of compositions of the invention for the relaxation of the IAS.

In this example, male Sprague-Dawley rats (250–300 g each) from Charles River were used. The rats were anesthetized intramuscularly with ketamine (90 mg/kg) and xylazine (9 mg/kg) and kept warm on a heated surgical table. All internal anal sphincter pressures (IASP) were measured with Millar catheter/transducers (MPC-500 mikrotip; Millar Instruments, Houston) on low pressure analyzers and blood pressure analyzers and recorded by DMSI software provided by Micro-Med (Louisville). Rats were provided with saline i.p. for rehydration due to the diuretic effects of the anesthesia and re-anesthetized as needed with approximately ⅓ the original dosage. In most experiments, the IASP was allowed to reach a stable baseline level prior to drug delivery. Drugs were delivered to the anal sphincter mainly via PE 20 tubing attached to the catheter(s) near the sensor (s) from 100 μl or 250 μl Hamilton syringes either manually or by infusion with a programmable Harvard automatic infusion pump.

Example 5

This example illustrates the effect of repeated or prolonged dosing of a nitric oxide donor (NTG) on the responsiveness of the rat IAS.

One issue with chronic or subchronic therapy with nitric oxide or nitric oxide donors such as NTG is the extent of any tachyphylaxis or tolerance to the relaxant effect of nitric oxide. Clinical studies have shown that the human cardiovascular system develops tolerance to nitric oxide donors. We have found that in the rat model, cardiovascular tolerance, as measured in vivo by the mean arterial blood pressure, also develops with repeated dosing of NTG. At the biochemical level, using in vitro assays, we have shown that NTG-induced increases in cGMP levels were attenuated dramatically in vascular smooth muscle. Thus, it seemed likely that the IAS would also develop tolerance to the effects of nitric oxide upon repeated or prolonged dosing.

Figure 6:
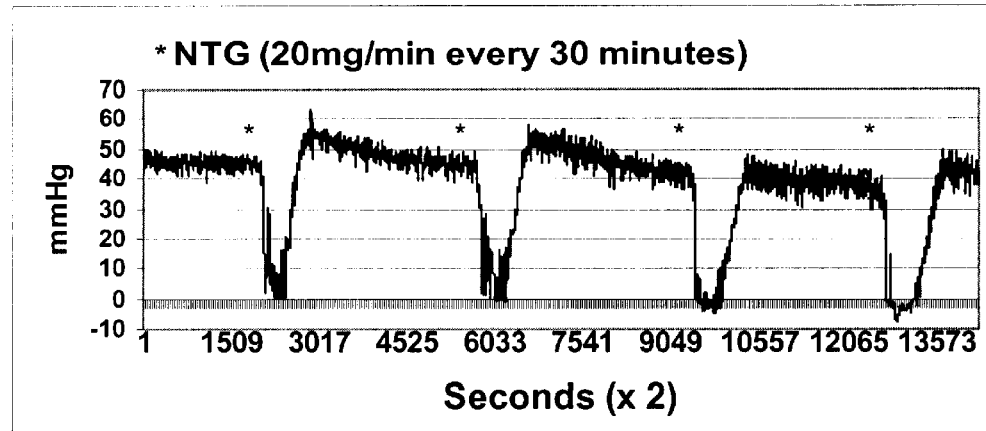
FIG. 6 illustrates the effect of NTG administered to the IAS as a bolus dose.

In FIG. 6, 0.1% NTG in 5% dextrose/water with 1% propylene glycol was administered in bolus doses directly to the IAS via a Hamilton syringe attached to a Harvard automatic infusion pump at 20 μg/min every 30 minutes. Each successive dose represented by asterisks produced a dramatic drop in resting IASP followed by a complete recovery to resting levels; a slight decline in resting pressures is observed over time, for most experiments, possibly due to the effects of anesthesia. Since each NTG administration was able to provide similar level and duration of pressure reduction, no nitrate related pressure tolerance was noted with repeated NTG administration.

Figure 7:
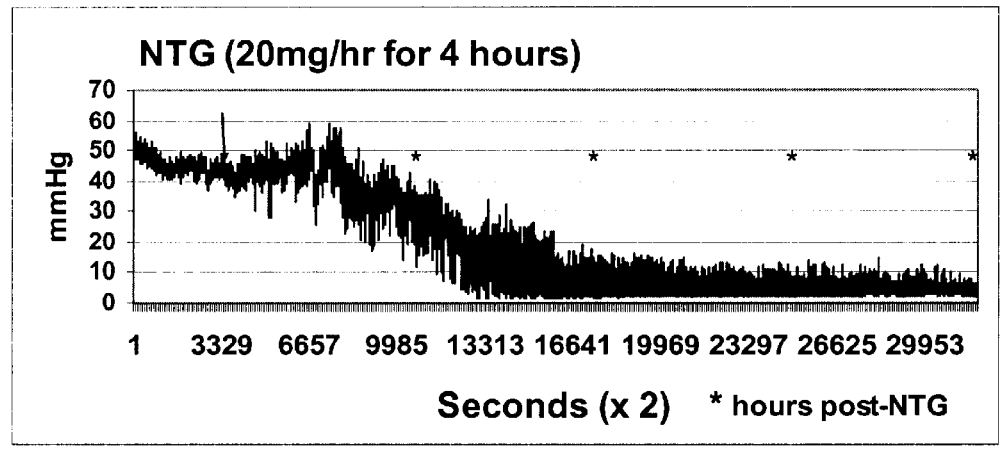
FIG. 7 illustrates the effect of NTG administered to the IAS by continuous infusion over 4 hours.

FIG. 7 demonstrates that a continuous infusion of NTG at 20 μg/hour produced a steady and sustained decline in resting IASP with no evidence of recovery in IASP during the entire treatment period, ruling out the incidence of tolerance, even after 4 hours of perfusion; asterisks indicate hours following initiation of NTG infusion. Similar results were obtained using a ten-fold higher dose of NTG. Since there was no rebound of pressure reduction with continuous NTG administration, no nitrate related pressure tolerance was noted with continuous NTG administration.

Surprisingly, we have found that tachyphylaxis to the relaxant effect of NTG on the IAS does not develop with repeated or prolonged dosing in vivo. Our in vitro studies have also found that NTG-induced increases in cGMP levels in the muscle of the IAS which were not as attenuated as those in vascular smooth muscle.

Example 6

This example illustrates the use of cyclic nucleotide analogs to affect IASP in the rat model.

Figure 8:
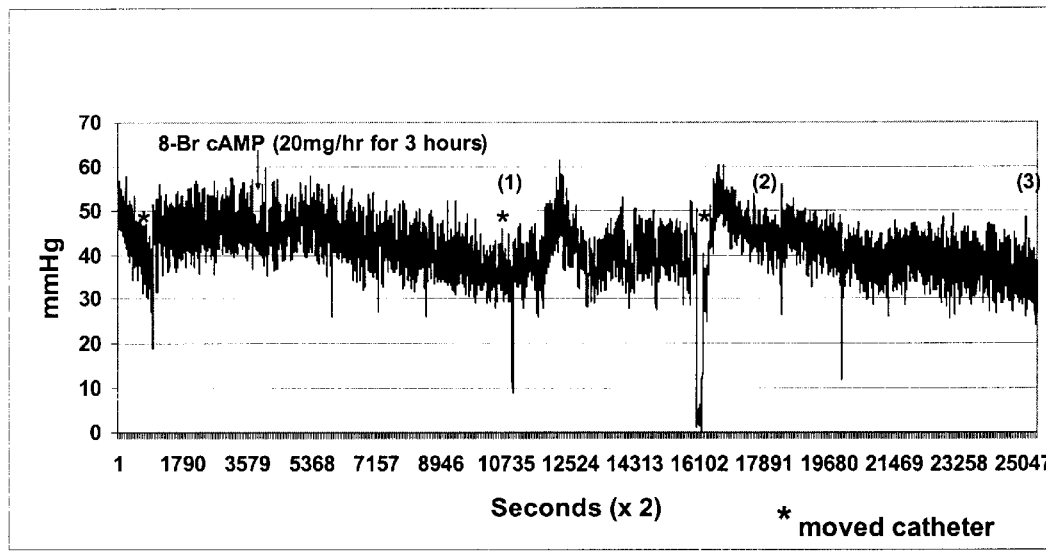
FIG. 8 illustrates the effect of 8-bromo cAMP infused to the IAS at 20 μg/hour for three hours.

8-bromo cAMP (0.1% in saline) was infused to the IAS at 20 μg/hour for 3 hours. Minimal pressure reduction was noted; this could due to the poor absorption of the 8-bromo cAMP from saline to the sphincter tissue during the study duration (see FIG. 8).

Figure 9:
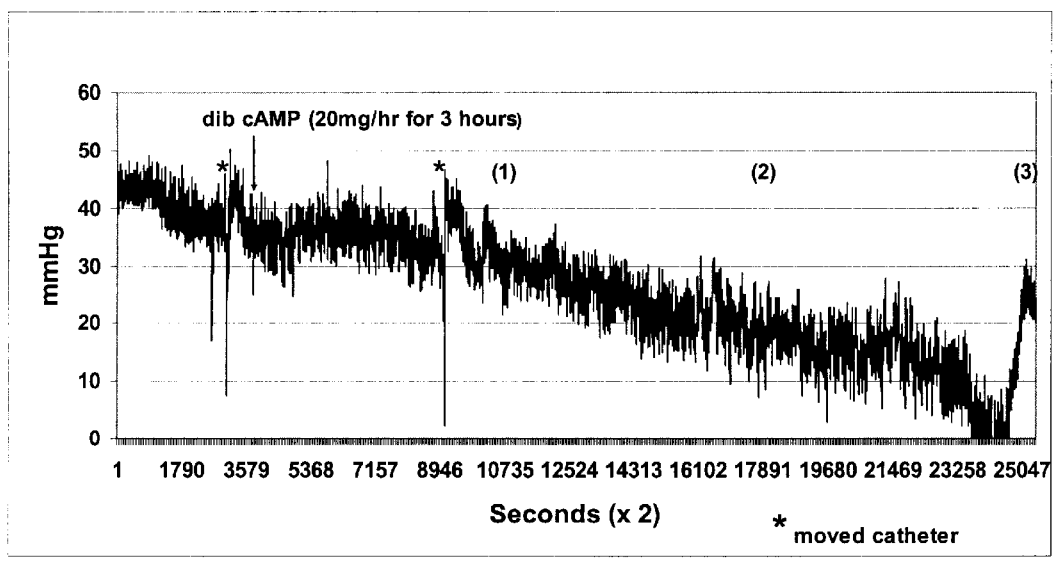
FIG. 9 illustrates the effect of dibutyryl cAMP infused to the IAS at 20 μg/hour for three hours.

Dibutyryl cAMP (0.1% in saline) was infused to the IAS at 20 μg/hour for 3 hours. A minor depression in IASP was noted (see FIG. 9). cGMP analogs also elicited very little depression of IASP, possibly due to the poor bioavailability through the in vivo topical dosage form.

Since increasing levels of cGMP and cAMP in the IAS with NTG or ISO resulted in an expected decrease in IASP, introduction of the aqueous-soluble 8-bromo and dibutyryl analogues of cGMP and cAMP were fully expected to also lower resting IASP in the rat model. Surprisingly, the cGMP analogs provided almost no effect on IASP (data not shown), whereas dibutyryl cAMP proved to be more efficacious in the rat model than the 8-bromo derivative as demonstrated in the following figures. These results may reflect differences in bioavailability of the analogs and/or direct effects of the butyrate moiety on smooth muscle relaxation.

Example 7

This example illustrates the varying ability of superoxide scavengers to potentiate the effect of nitric oxide/nitric oxide donors in vivo.

The ability of superoxide scavenger superoxide dismutase (SOD) to potentiate the relaxing effects of NTG by prolonging the half-life of nitric oxide (NO) was examined using the rat model. NO, produced from the enzymatic degradation of NTG within cells, has a half-life of only a few seconds before it is acted upon by oxygen radicals such as the superoxide anion to form peroxynitrite (Weller, 1997). Perfusion of the anal sphincter with SOD prior to NTG treatment, theoretically should remove superoxide from the equation, providing a longer half-life for NO in the tissue and resulting in more sustained cGMP levels, potentiating the NTG-induced relaxation of the IAS.

Vehicle (20 μl of 5% dextrose/water with 10% propylene glycol) was delivered to the IAS followed in 30 minutes by a 200 μg bolus delivery of superoxide dismutase (SOD) in vehicle, followed 15 minutes later with a bolus dose of 200 μg NTG in the same vehicle. A significant potentiation of NTG effect, e.g. increasing the duration of action on reducing anal sphincter was observed (see FIG. 10). This result indicates that the activity of the NO donor in the presence of a superoxide anion scavenger is enhanced.

Vehicle (20 μl of 5% dextrose/water with 10% propylene glycol) was delivered to the IAS followed in 30 minutes by a 200 µg bolus delivery of NTG in vehicle, followed 15 minutes later with a bolus dose of 20 µg SOD. No significant potentiation of NTG was observed suggesting that the potentiation effect of SOD is most pronounced when administered prior to NTG (see FIG. 11). This result suggests that the NTG-derived NO has already dissipated from the tissue.

Surprisingly, the synthetic superoxide scavenger Mn (III) tetrakis (4-benzoic acid) porphyrin chloride (MnTBAP), did not demonstrate significant NO enhancing activity in this model.

Figure 10:
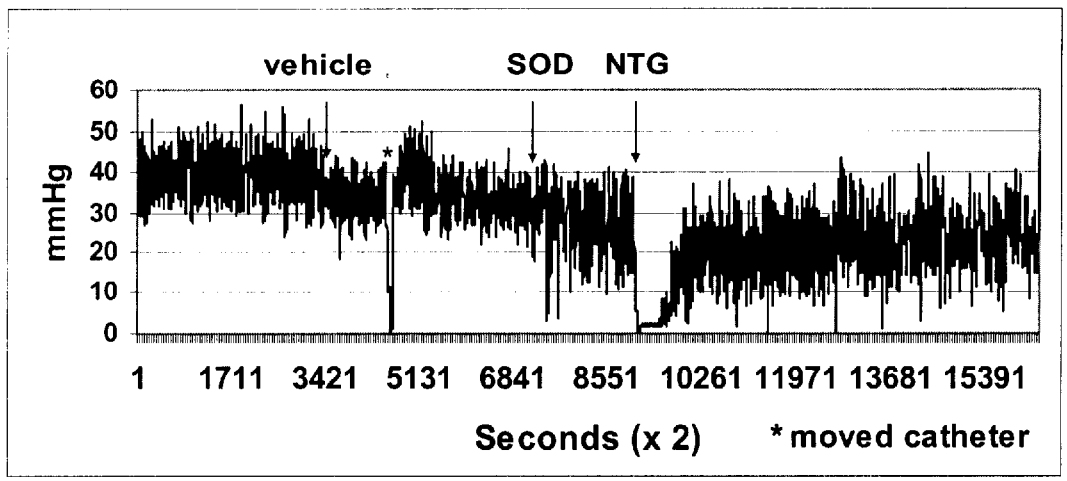
FIG. 10 illustrates the effect of a bolus delivery of SOD (200 μg) to the IAS, followed by a bolus dose of NTG (200 μg) in the same vehicle.
Figure 11:
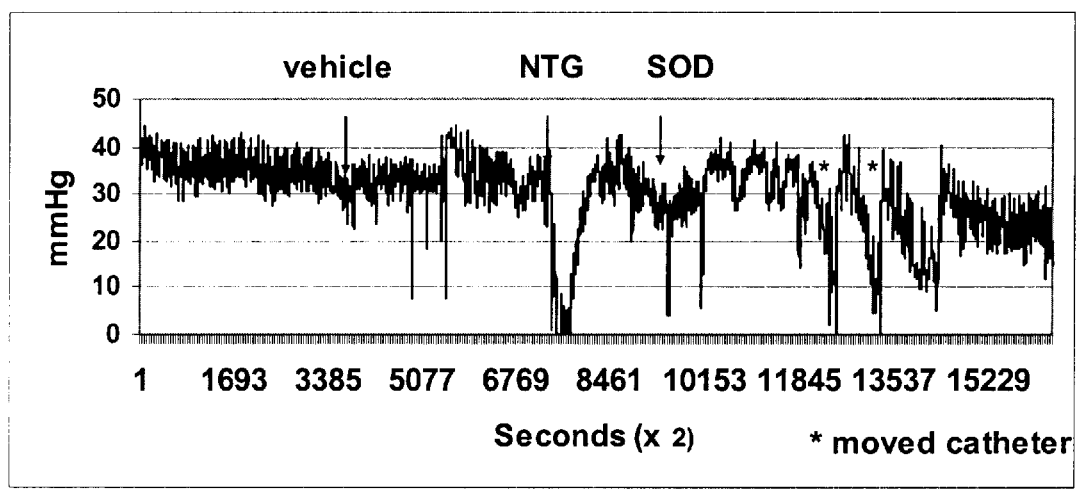
FIG. 11 illustrates the effect of a bolus delivery of NTG (200 μg) to the IAS, followed by a bolus dose of SOD (200 μg) in the same vehicle.

Further, as FIGS. 10 and 11 demonstrate, SOD alone has little effect on IASP since the resting IAS has low endogenous levels of NO to act upon by superoxide anion.

Example 8

This example illustrates the potentiation of NTG in the rat model by PDE V inhibitor blockage of the cGMP-specific PDE activity.

Figure 12:
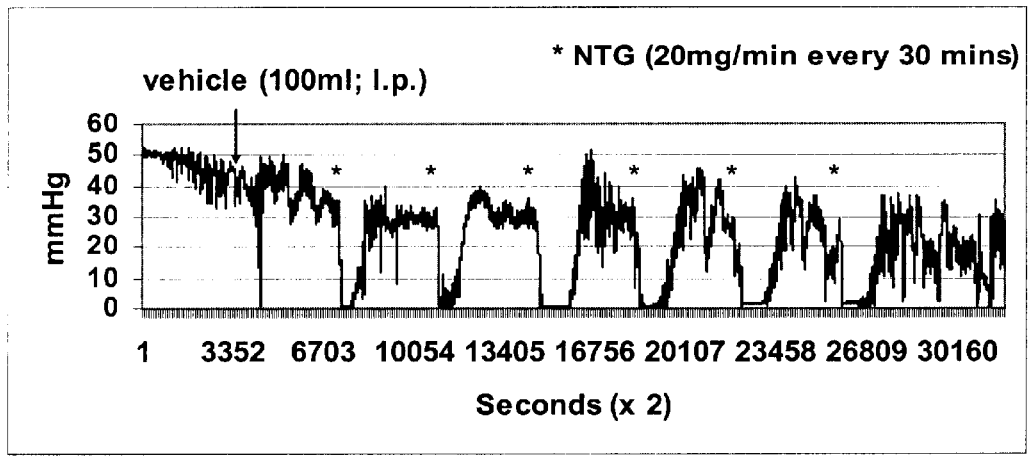
FIG. 12 illustrates the effect on the IAS of a vehicle injection followed after 30 minutes by bolus doses of NTG.

Zaprinast:

The vehicle, 1-methyl 2-pyrollidinone (1M2P) was injected intraperitoneal (i.p.). (100 µl), 30 minutes prior to bolus doses of NTG (20 µg/min every 30 minutes). The duration of depression of IASP due to NTG was constant with each dose (see FIG. 12).

Figure 13:
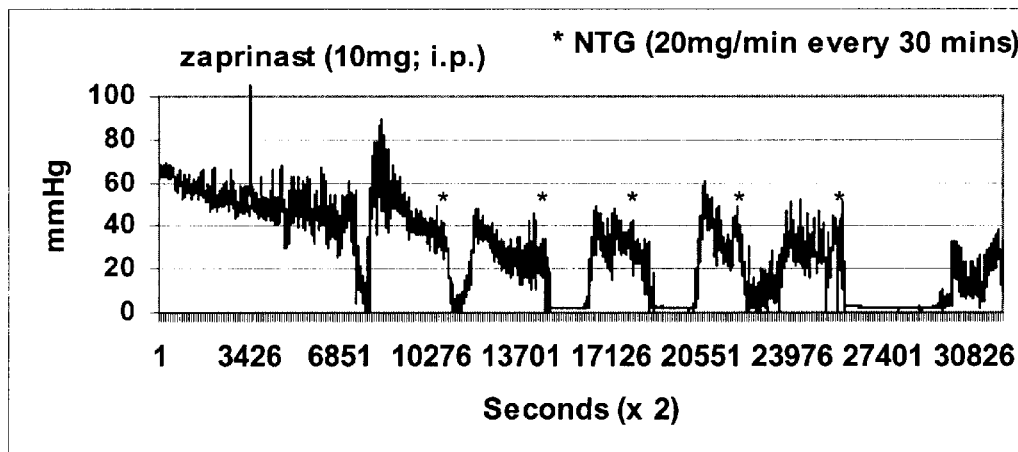
FIG. 13 illustrates the effect on the IASP of an i.p. injection of zaprinast followed by bolus doses of NTG applied topically to the IAS.

Zaprinast (10 mg in 100 µl 1M2P) was injected i.p. 30 minutes prior to bolus doses of NTG (20 µg/min every 30 minutes). There was an increasing duration of IASP depression with consecutive doses of NTG demonstrating potentiation of NTG by a selective PDE V inhibitor (see FIG. 13).

Figure 14:
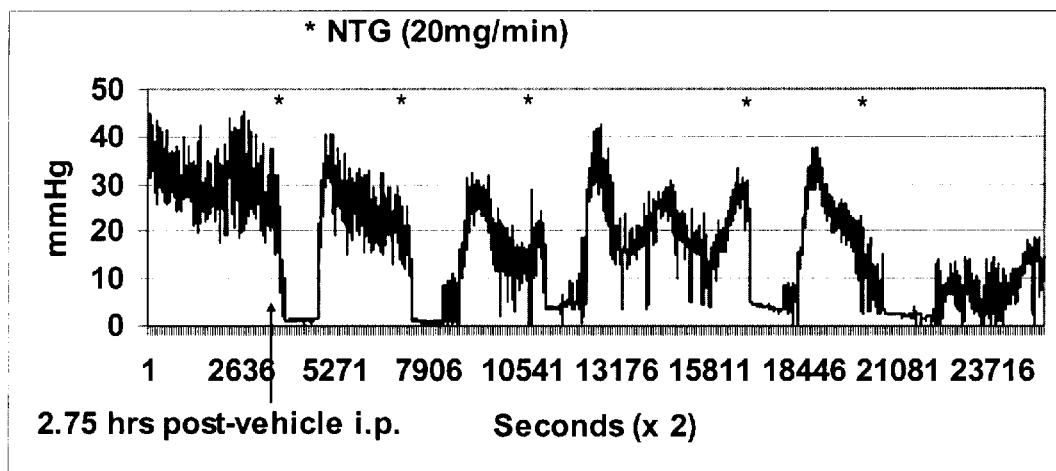
FIG. 14 illustrates the effect on the IASP of a bolus dose of NTG applied topically to the IAS, wherein the first NTG dose is provided at 2.75 hours after a vehicle injection.

The vehicle, 1-methyl 2-pyrollidinone (1M2P) was injected intraperitoneal (i.p.). (100 µl), followed after 2.75 hours by the first dose of NTG (20 µg/min every 30 minutes). The duration of depression of IASP was consistent with each NTG dose (see FIG. 14).

Figure 15:
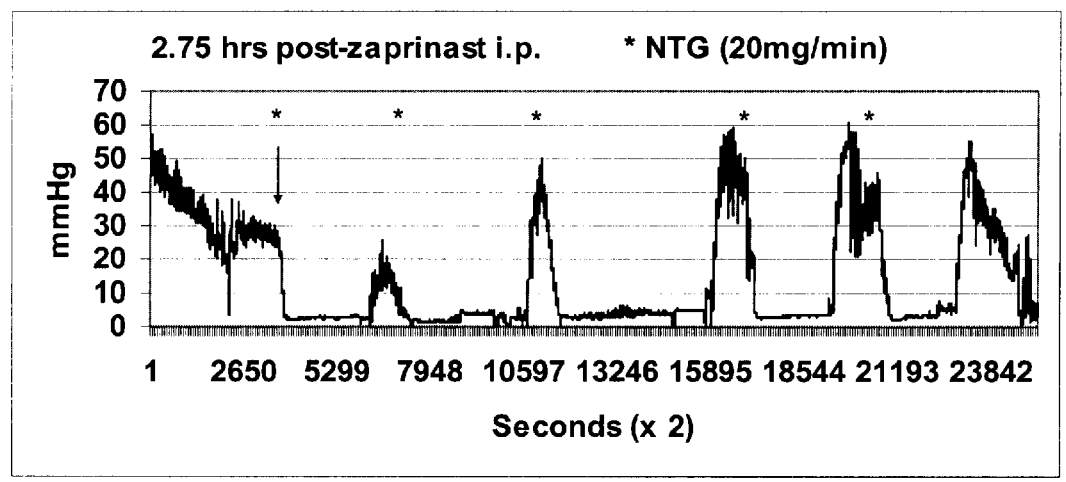
FIG. 15 illustrates the effect on the IASP of an i.p. injection of zaprinast followed by bolus doses of NTG, wherein the first NTG dose is provided at 2.75 hours after zaprinast injection.

Zaprinast (10 mg in 100 µl 1M2P) was injected i.p. 2.75 hours prior to bolus doses of NTG (20 µg/min every 30 minutes). The duration of depression of IASP continued to increase with each NTG dose and peaked at around 3.5–4 hours and decreased with additional doses of NTG. This study suggests that an i.p. dose of zaprinast reaches maximal levels in the IAS between 3.5–4 hours and causes potentiation with NTG (see FIG. 15).

These results show that potentiation of NTG activity can be achieved by agents protecting from PDE degradation the cGMP formed through NO activation of guanylyl cyclase.

Dipyridamole

Figure 16:
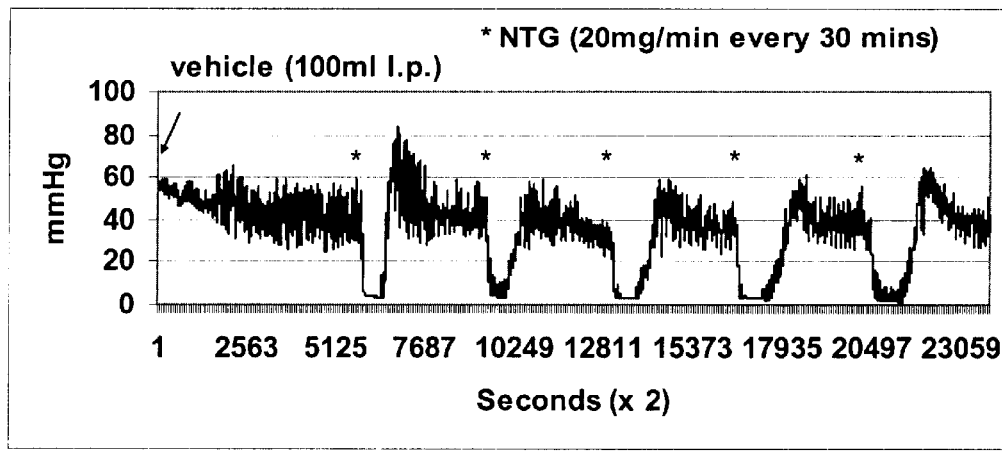
FIG. 16 illustrates the effect on the IAS of a vehicle injection followed after 50 minutes by bolus doses of NTG.

The vehicle, 1-methyl 2-pyrollidinone (1M2P) was injected i.p. (100 µl), 50 minutes prior to bolus doses of NTG (20 µg/min every 30 minutes). The duration of depression of IASP due to NTG was constant with each dose (see FIG. 16).

Figure 17:
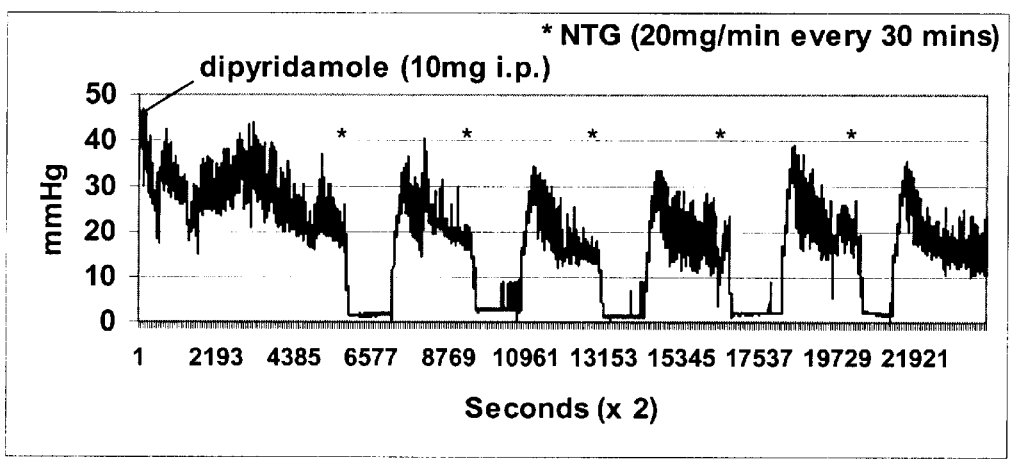
FIG. 17 illustrates the effect on the IAS of PDE V inhibitor, dipyridamole injected i.p. 50 minutes prior to bolus doses of NTG.

Dipyridamole (10 mg in 100 µl 1M2P) was injected i.p. 50 minutes prior to bolus doses of NTG (20 µg/min every 30 minutes). The duration of depression of IASP due to NTG was constant with each dose and approximately twice that for the vehicle-treated rat (see FIG. 17).

MBCQ

Figure 18:
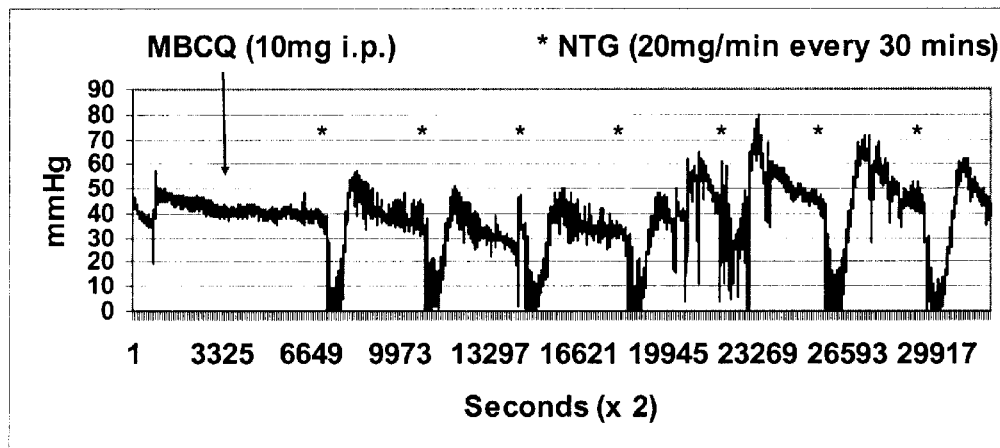
FIG. 18 illustrates the effect on the IASP of PDE V inhibitor MBCQ injected i.p. 30 minutes prior to bolus doses of NTG.

MBCQ (10 mg in 100 µl 1M2P) was injected i.p. 30 minutes prior to bolus doses of NTG (20 µg/min every 30 minutes). No noticeable potentiation of NTG was observed with this PDE V inhibitor in this experiment (see FIG. 18). Bioavailability of MBCQ could be the cause of the minimal effect seen with this compound.

Whereas dipyridamole demonstrated less striking potentiation with NTG, the most potent of the PDE V inhibitors under in vitro conditions, MBCQ, did not demonstrate significant activity, potentially due to diminished bioavailability of this drug in the in vivo model (data not shown).

Example 9

This example illustrates the effect of non-selective β-adrenergic agonists using isoproterenol. These agonists activate adenyl cyclase, thereby increasing cAMP levels, and act on the IASP through the direct smooth muscle relaxing activity of cAMP.

Figure 19:
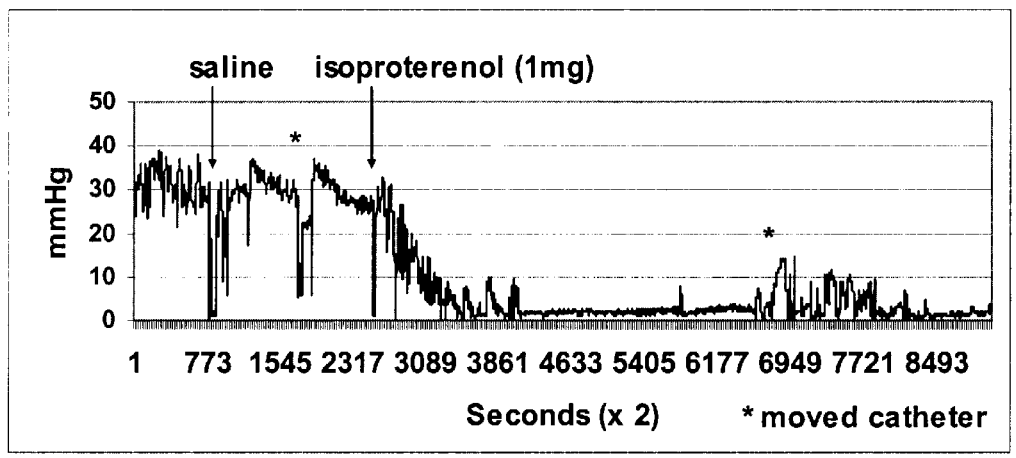
FIG. 19 illustrates the effect on the IASP of β-agonist isoproterenol delivered to the IAS 30 minutes after saline alone.

A bolus dose of 200 µg isoproterenol produced a dramatic drop in IASP eliminating significant pressure readings by the catheter/transducer in fact, isoproterenol proved to be a very potent IAS relaxant and had to be titred down, in another study, to a continuous dose of 0.2 µg/hour in order to avoid significant drops in IASP (see FIG. 19).

Example 10

This example illustrates the effect of $\beta_2$-agonists on the IASP.

Figure 20:
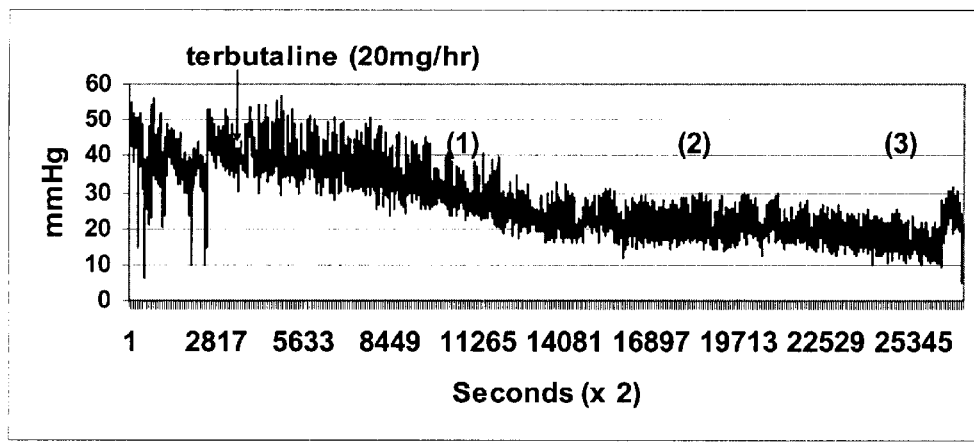
FIG. 20 illustrates the effect on the IASP of $\beta_2$-agonist terbutaline in saline infused continuously at 20 μg/hour.

The $\beta_2$-agonist, terbutaline (in saline) was infused continuously at 20 µg/hour. A steady and sustained decline in IASP over the 3 plus hours of infusion (FIG. 4n, 20) resulted. The significant drop in IASP throughout the experiment reached a plateau between 1.5 and 2 hours post initiation of treatment.

This sustained, however moderate, drop in IASP is considered desirable for prolonging the increased blood flow to the anoderm necessary for healing anal fissures, without inducing a complete relaxation of the IAS which might result in temporary incontinence.

Figure 21:
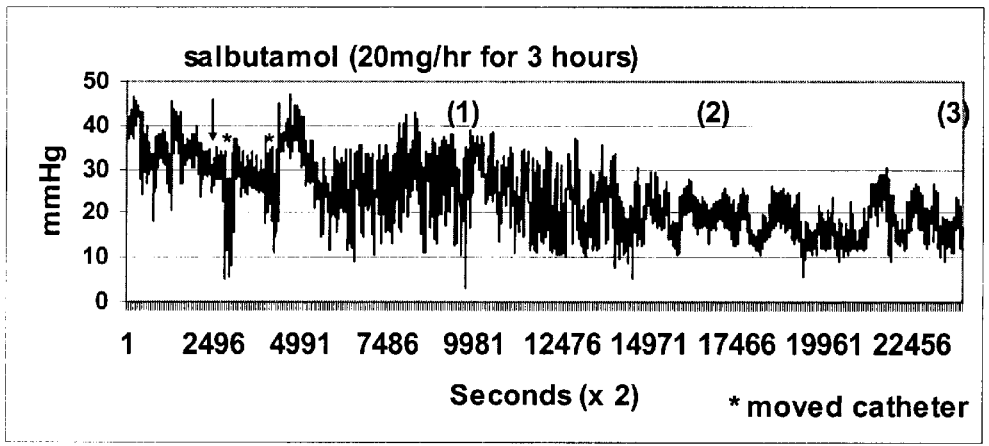
FIG. 21 illustrates the effect on the IASP of $\beta_2$-agonist salbutamol in saline infused continuously at 20 μg/hour.

The $\beta_2$-agonist, salbutamol (in saline) was infused continuously at 20 µg/hour and demonstrated a significant drop in IASP throughout the experiment similar to terbutaline (see FIG. 21).

Example 11

This example illustrates the effects of cAMP levels on the IASP and the effects of PDE IV inhibitor blockage of the cAMP-specific PDE activity in the rat model.

Effects of Rolipram

Figure 22:
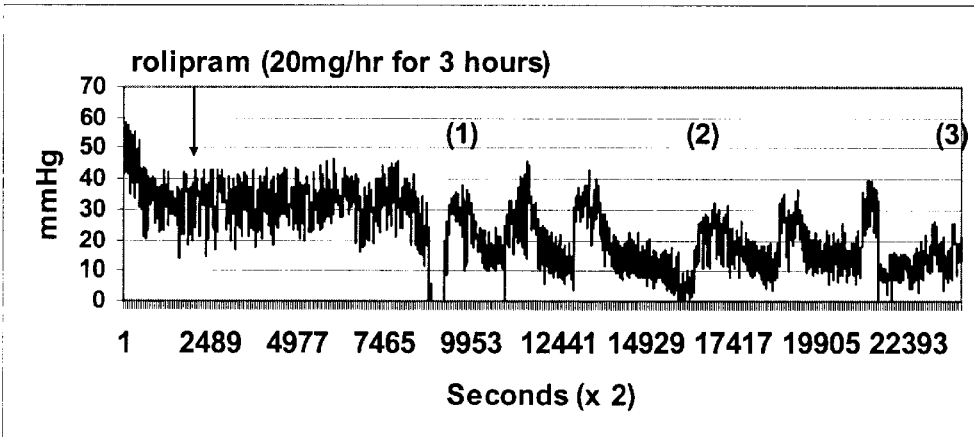
FIG. 22 illustrates the effect on the IASP of PDE IV inhibitor rolipram in DMSO/acetone/olive oil infused continuously at 20 μg/hour.

The PDE IV inhibitor rolipram, in 5% DMSO/Acetone:Olive oil 1:1 was continuously infused at 20 µg/hour rate. A pattern including significant drops in IASP followed by shorter recovery phases occurred prior to 1 hour after initiating the drug infusion (see FIG. 22).

Etazolate Potentiation of Salbutamol

Figure 23:
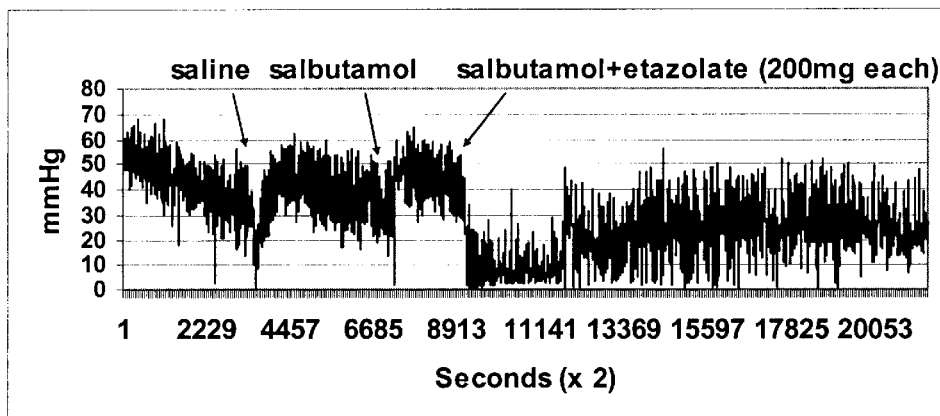
FIG. 23 illustrates a bolus dose of salbutamol followed by a single bolus dose of salbutamol and PDE IV inhibitor etazolate.

Delivery of 200 µg of salbutamol in saline to the IAS produced no short-term effects on the IASP; however a subsequent treatment with salbutamol plus the PDE IV inhibitor etazolate, also at 200 µg in saline, produced a dramatic and sustained drop in IASP, suggesting a potentiation effect of a $\beta_2$-agonist with a PDE IV inhibitor on anal sphincter pressure reduction (see FIG. 23).

Figure 24:
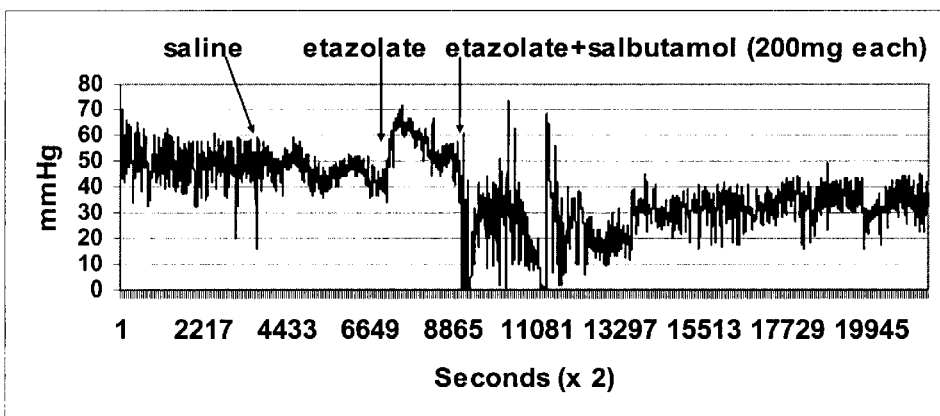
FIG. 24 illustrates a bolus dose of etazolate followed by a single bolus dose of salbutamol and etazolate.

This experiment is similar to that described above for FIG. 23, however the order of the delivery of the drugs was reversed. The results were similar (see FIG. 24).

Smooth muscle relaxation is caused by agents that elevate cAMP levels via phosphorylation of myosin light chain kinase by cAMP-dependent protein kinase (PKA). PDE type IV inhibitors prevent degradation of cAMP by cAMP-specific PDE. As seen with the above PDE IV inhibitor etazolate potentiation of the effects of the $\beta_2$-adrenergic agonist, salbutamol, potentiation of agents which activate adenylyl cyclase, can be achieved with PDE type IV inhibitors.

Effects of RO-20-1724

Figure 25:
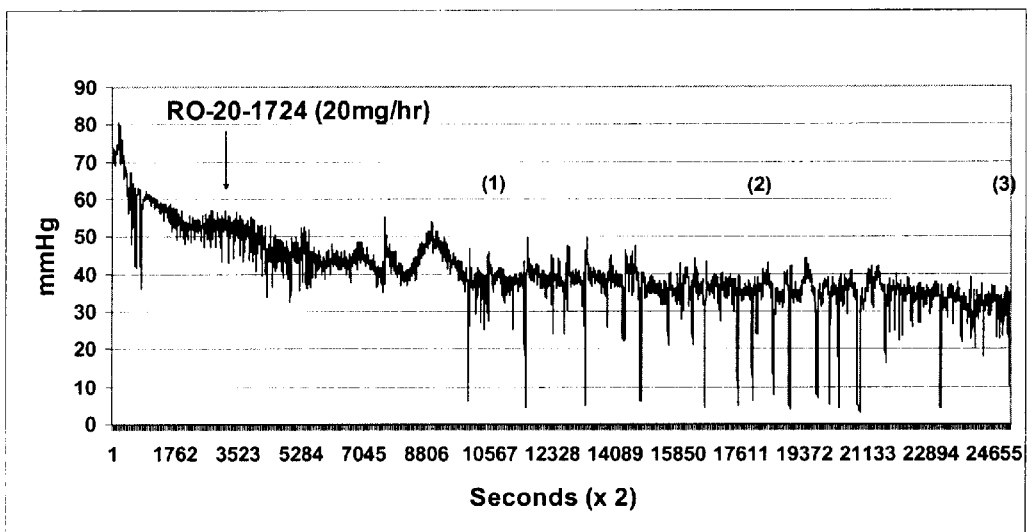
FIG. 25 illustrates the effect on the IASP of PDE IV inhibitor Ro 20-1724 in DMSO/acetone/olive oil infused continuously at 20 μg/hour.

The PDE IV inhibitor RO-20-1724 was infused at 20 µg/hour in the vehicle 5% DMSO/Acetone:Olive oil 1:1. The drop in IASP was minimal suggesting either lack of bioavailability of the drug from the current route of administration (see FIG. 25).

Effects of Forskolin

Figure 26:
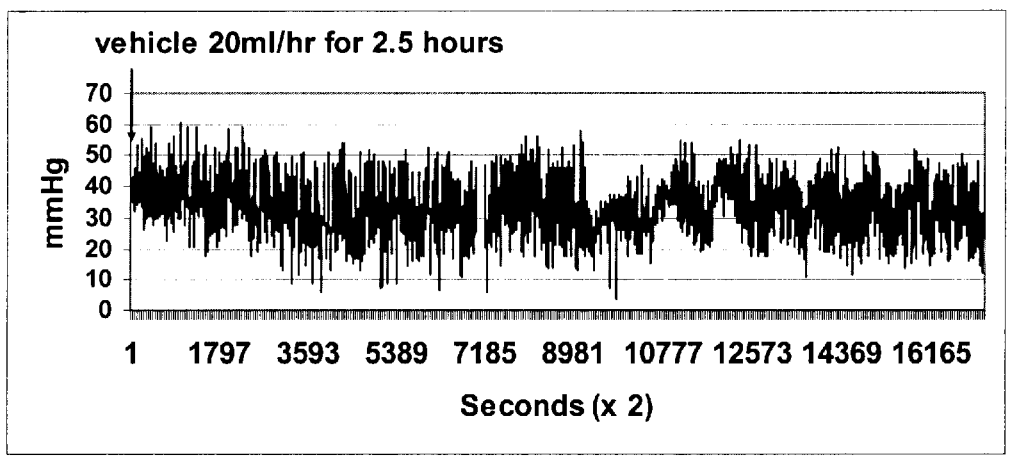
FIG. 26 illustrates a vehicle control for the treatments provided in FIG. 27.
Figure 27:
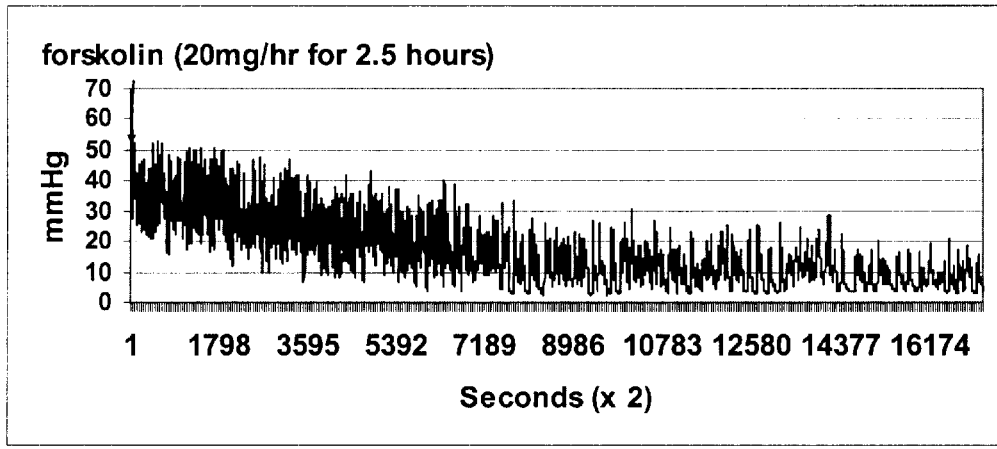
FIG. 27 illustrates the effect on the IASP of the specific adenyl cyclase activator forskolin, in DMSO/acetone/olive oil infused continuously at 20 μg/hour.

The specific adenyl cyclase activator forskolin, was infused at 20 µg/hour in the vehicle 5% DMSO/Acetone:Olive oil 1:1. A significant and sustained drop in IASP was observed (see FIGS. 26 (control) and 27). This experiment clearly demonstrates the contribution of cAMP in inducing relaxation of the internal anal sphincter.

Example 12

This example illustrates the use of α-adrenergic antagonists to reduce IASP in the rat model.

Figure 28:
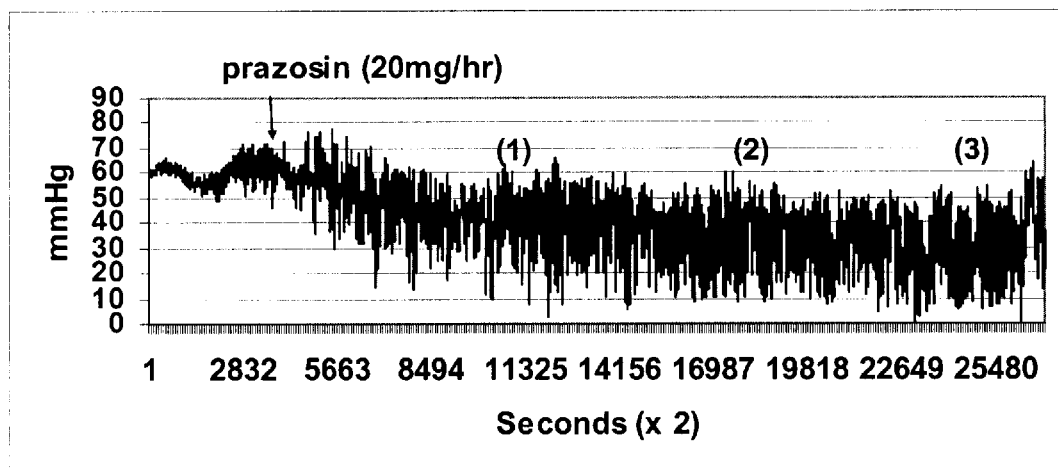
FIG. 28 illustrates the effect on the IASP of the $\alpha_1$-blocker, prazosin, in DMSO/acetone/olive oil infused continuously at 20 μg/hour.

The $\alpha_1$-blocker, prazosin in 5% DMSO/Acetone:Olive oil 1:1 was infused at 20 µg/hour. A significant and sustained drop in IASP that plateaued after 1 hour was observed suggesting that the increase of cAMP level leads to relaxation of internal anal sphincter pressure (see FIG. 28).

Example 13

This example illustrates the effect of non-selective PDE Inhibitors on IASP in the rat model.

Figure 29:
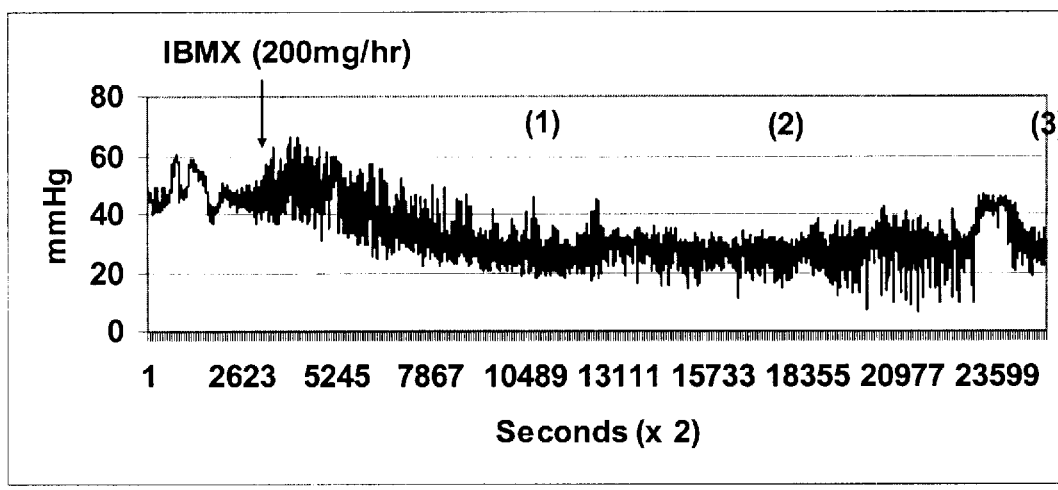
FIG. 29 illustrates the effect on the IASP of the nonspecific PDE inhibitor IBMX, in DMSO/acetone/olive oil infused continuously at 200 μg/hour.

Isobutyl methylxanthine (IBMX) in 5% DMSO/Acetone:Olive oil 1:1 was infused at 200 µg/hour. A significant and sustained drop in IASP that leveled off at 1 hour after initiation of the infusion was observed (see FIG. 29).

Figure 30:
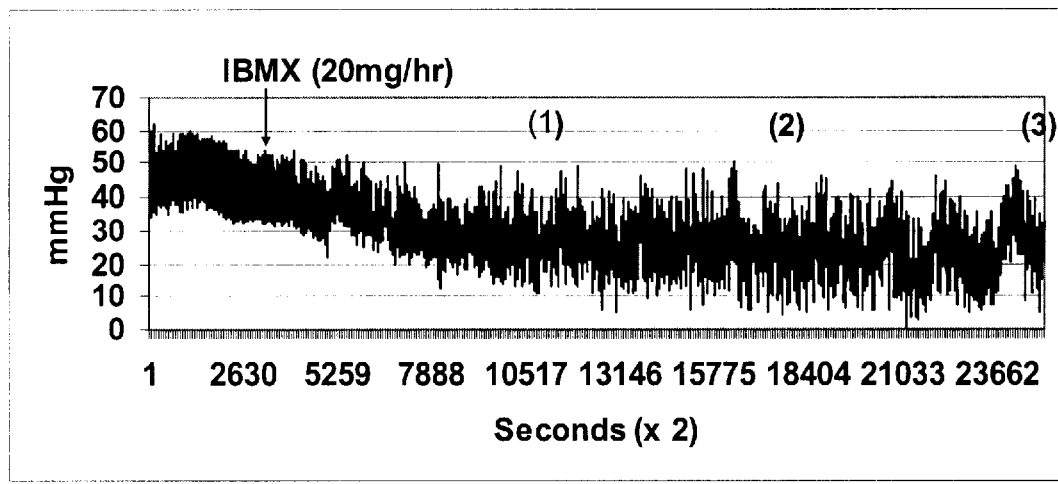
FIG. 30 illustrates the effect on the IASP of the nonspecific PDE inhibitor IBMX, in DMSO/acetone/olive oil infused continuously at 20 μg/hour.

Isobutyl methylxanthine (IBMX) in 5% DMSO/Acetone:Olive oil 1:1 was infused at a lower dose, i.e. 20 µg/hour. The results were similar as for the experiment described in FIG. 29 (see FIG. 30).

The non-selective PDE inhibitor, IBMX is thought to act on smooth muscle by a number of potential mechanisms including: 1) PDE inhibition and increasing cAMP levels; 2) effects on intracellular calcium concentration; 3) effects on membrane hyperpolarization; 4) uncoupling of increased calcium levels with muscle contractility; and 5) adenosine receptor antagonism (Goodman & Gilman's "The Pharmacological Basis of Therapeutics" $9^{th}$ edition. Section IV-Autocoids; Drug Therapy of Inflammation).

Example 14

This example illustrates the use of K+-ATP Channel Openers to relax the IAS.

The $K^+$-ATP channel openers, minoxidil and diazoxide, induce hyperpolarization of the cell membranes of smooth muscle, and thereby inactivate voltage-gated $Ca^{2+}$ channels.

Figure 31:
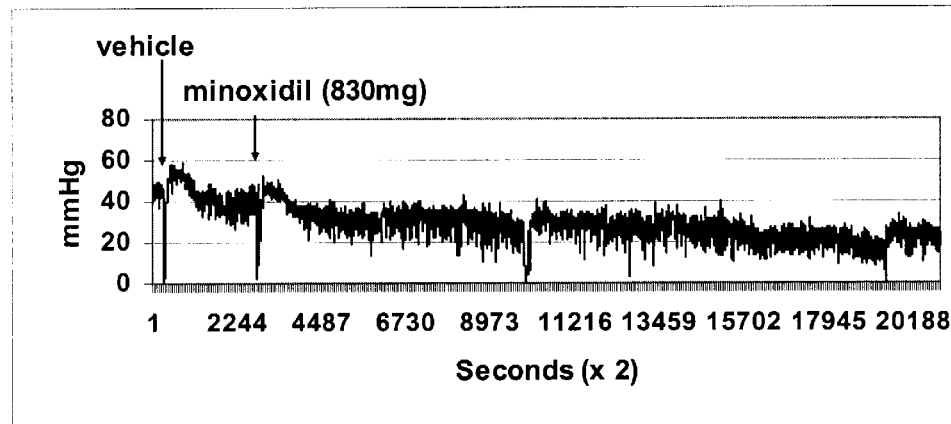
FIG. 31 illustrates the effect on the IASP of a single bolus dose of the $K^+$-ATP channel opener minoxidil in propylene glycol/water.

Minoxidil (830 µg in 20 µl 62.5% propylene glycol/water) was delivered to the IAS. A significant and sustained drop in IASP was observed shortly after delivery of the drug (see FIG. 31).

Figure 32:
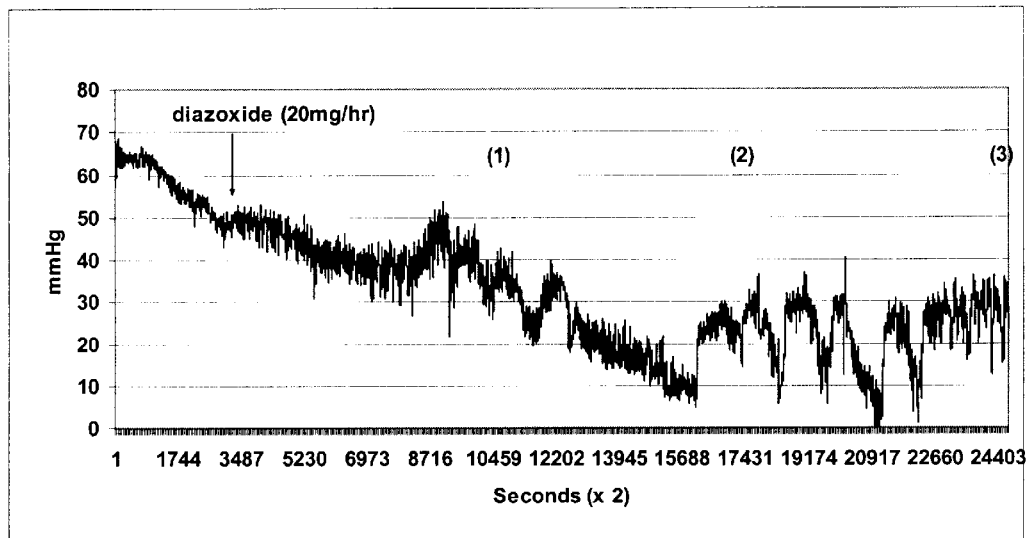
FIG. 32 illustrates the effect on the IASP of the $K^+$-ATP channel opener diazoxide, in DMSO/acetone/olive oil infused continuously at 20 μg/hour.

Diazoxide in 5% DMSO/Acetone:Olive oil 1:1 was infused at 20 µg/hour. A dramatic drop in IASP was observed for the duration of the experiment (see FIG. 32).

Example 15

This example illustrates the use of $Ca^{2+}$-channel blockers

Figure 33:
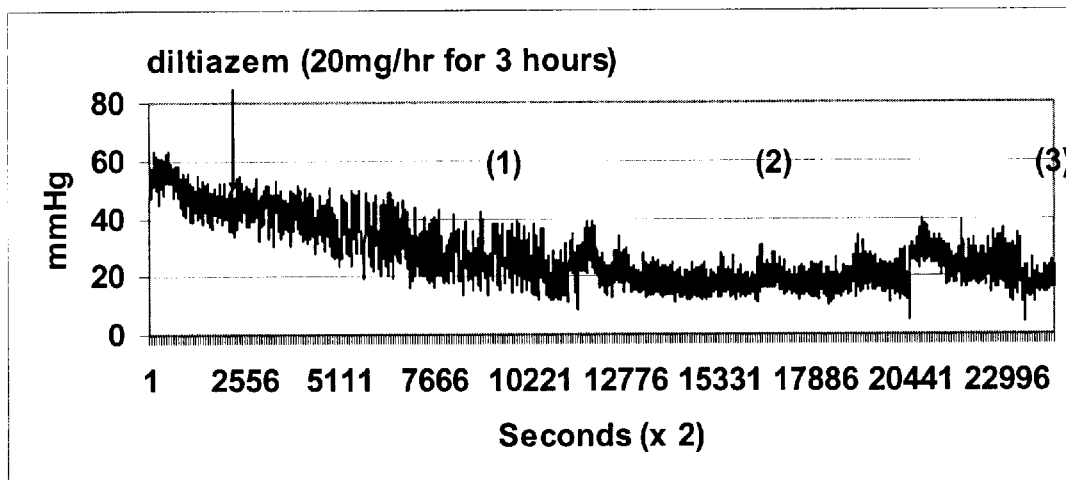
FIG. 33 illustrates the effect on the IASP of the $Ca^{+2}$-channel blocker diltiazem in saline infused continuously at 20 μg/hour.

Diltiazem in saline was infused at 20 µg/hour. The drug produced a dramatic and sustained drop in IASP for the duration of the experiment (see FIG. 33).

Figure 34:
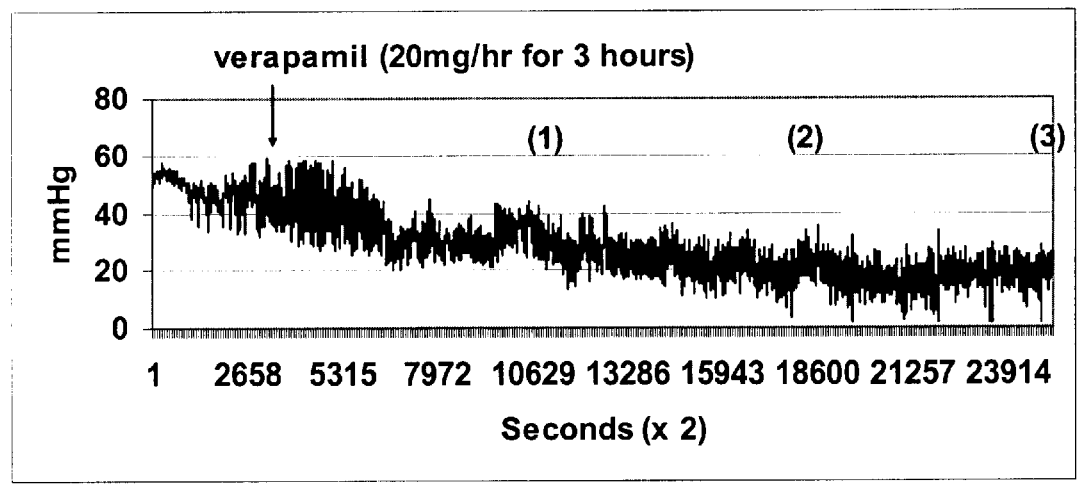
FIG. 34 illustrates the effect on the IASP of the $Ca^{+2}$-channel blocker verapamil in saline infused continuously at 20 μg/hour.

Verapamil in saline was infused at 20 µg/hour. The drug produced a dramatic and sustained drop in IASP for the duration of the experiment (see FIG. 34).

Example 16

This example illustrates the use of sympathetic nerve terminal destroyers to achieve a long term reduction in IASP in the rat model following a short term administration of the active agent.

Neurogenic tone of the IAS is largely due to sympathetic adrenergic innervation; norepinephrine released by the nerves acts on $\alpha_1$-adrenergic receptors to contract smooth muscle. Earlier reports suggested that α-blockers reduced anal pressure in man (Speakman, C. T., *Dig Dis Sci* 38(11) :1961–9 (1993); Parks, A. G., *Gut* 10(8): 674–7 (1969)). Recent clinical trials using one of the most potent toxins known, botulinus toxin, produced by *Clostridium botulinum*, have demonstrated success in healing anal fissures after multiple injections of the toxin directly into the IAS. Botulinus toxin presumably relaxes the IAS through its action of blocking acetylcholine (ACH) release from cholinergic pre-synaptic fibers (Kao, I., et al., *Science* 193, 1256–8 (1976)). However, cholinergic innervation of the IAS is not thought to contribute significantly to IAS tone. We decided to use a drug that can be applied topically to the IAS, and that destroys adrenergic nerve terminals, thereby blocking the actions of norepinephrine in maintaining sphincter tone.

Figure 35:
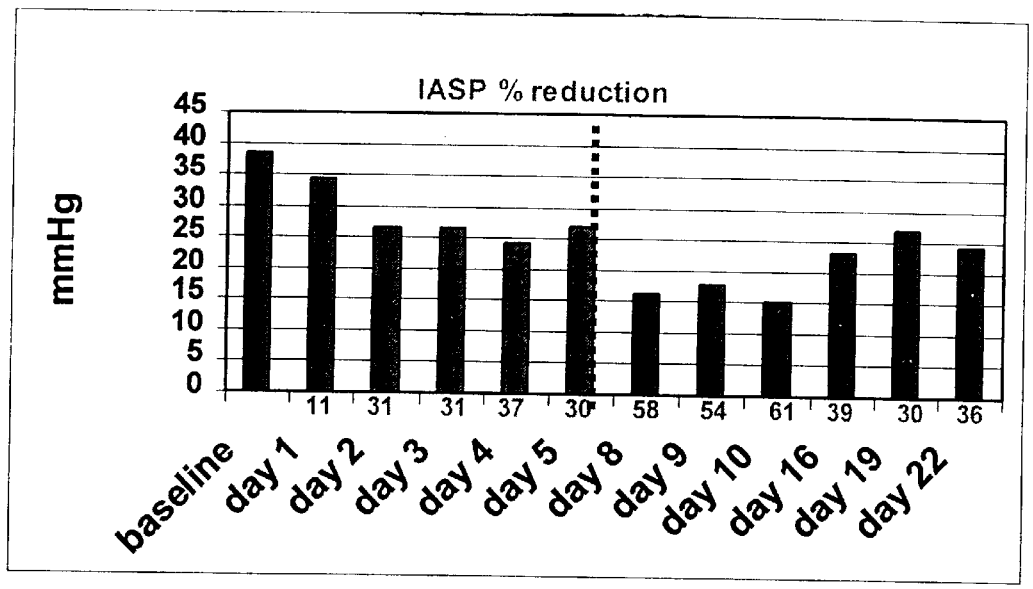
FIG. 35 illustrates the effect on the IASP of the sympathetic nerve terminal destroyer 6-hydroxydopamine when administered to the IAS in bolus doses of 200 μg per day for 5 days.

6-hydroxydopamine in saline was delivered to the IAS in bolus doses of 200 µg to a rat each day for 5 days. The IASP was measured over three weeks. A continuous drop in IASP was noted through day 16, 11 days after termination of the treatment. By day 19 a partial recovery in IASP was observed, and by day 22 the average IASP was 36% below the original baseline pressure (see FIG. 35).

Thus, treatment with 6-hydroxydopamine (6-OHDA), resulted in a prolonged reduction in IASP over at least a 3 week period following 5 daily topical doses of 200 µg in saline to the rat IAS.

Example 17

This example illustrates the effects of a PDE III/IV inhibitor on IASP under a variety of experimental conditions.

Figure 36:
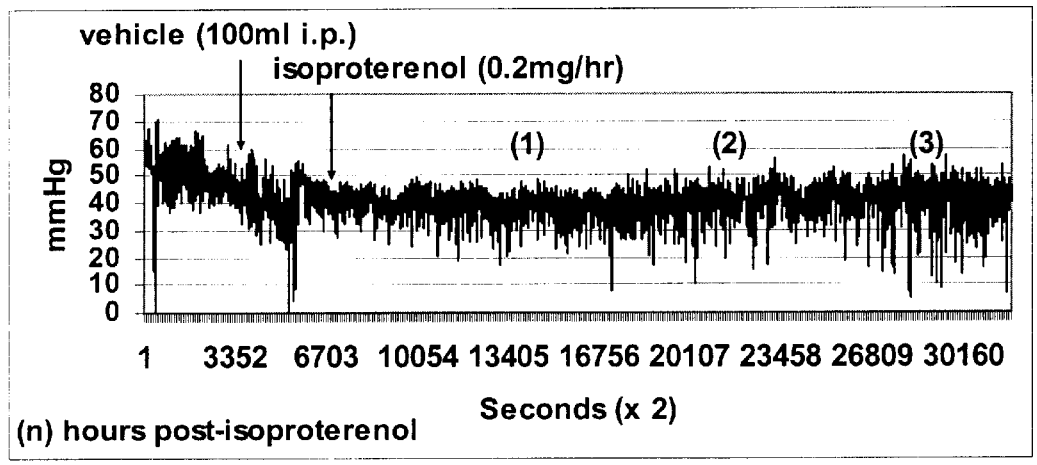
FIG. 36 illustrates the effect on the IASP of a control vehicle i.p injection of 1-methyl-2-pyrollidinone followed after 30 minutes by continuous infusion of a sub-threshold dose of isoproterenol in saline (0.2 μg/hour).
Figure 37:
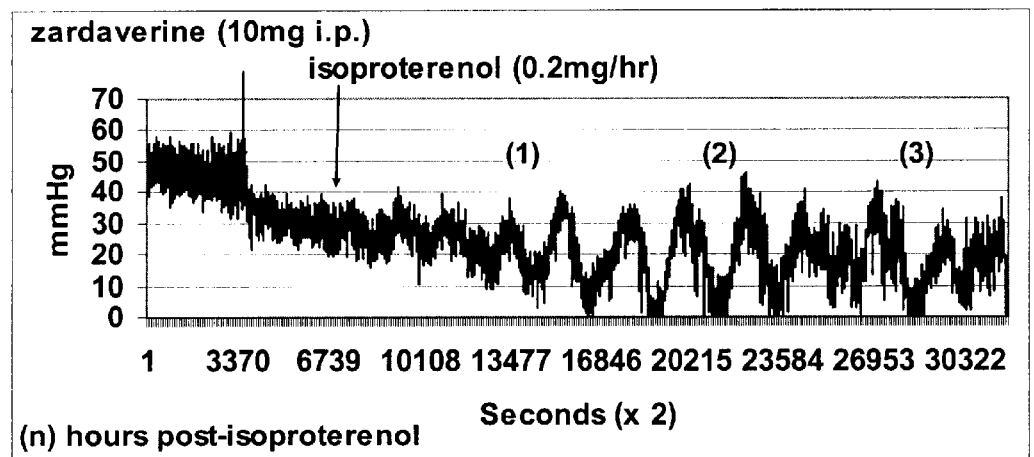
FIG. 37 illustrates the effect on the IASP of the PDE III/IV inhibitor zardaverine when injected i.p. (10 mg in vehicle) followed after 30 minutes by a continuous infusion of isoproterenol.

This experiment serves as a control for the experiment described in FIG. 37. An i.p. injection of 100 µl 1M2P was followed in 30 minutes by a continuous infusion of isoproterenol in saline at 0.2 µg/hour. This sub-threshold dose of isoproterenol had no significant effect on lowering IASP (see FIG. 36).

The PDE III/IV inhibitor, zardaverine (10 mg in 100 µl 1M2P) was injected i.p. followed in 30 minutes by a continuous infusion of isoproterenol in saline at 0.2 µg/hour. A rapid drop in IASP was noted immediately after the i.p. injection of zardaverine, and a sustained decrease in average IASP followed isoproterenol infusion. A continuous slow wave pattern of decreasing and increasing IASP was observed after isoproterenol infusion (see FIG. 37).

Figure 38:
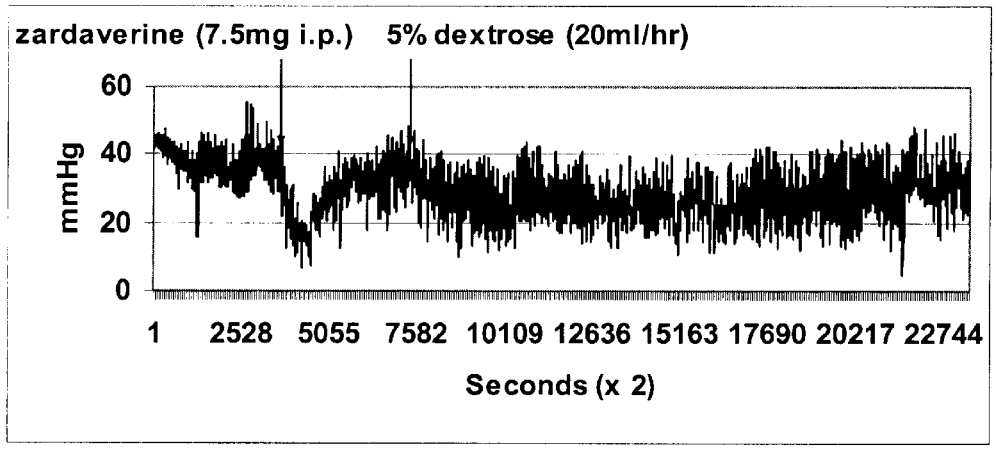
FIG. 38 illustrates the effect on the IASP of the PDE III/IV inhibitor zardaverine when injected i.p. (7.5 mg in vehicle) followed after 30 minutes by a continuous infusion of 5% dextrose.

The PDE III/V inhibitor, zardaverine (7.5 mg in 100 µl 1M2P) was injected i.p. followed in 30 minutes by a continuous infusion of 5% dextrose at 20 µl/hour. The zardaverine injection produced a rapid but transient drop in IASP that soon returned to normal baseline levels. The subsequent infusion of 5% dextrose had no effect on lowering the IASP (see FIG. 38).

Figure 39:
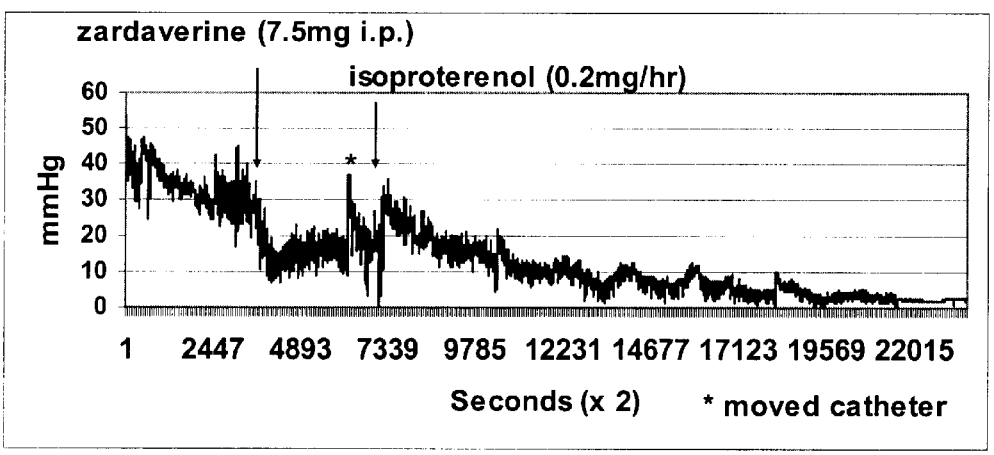
FIG. 39 illustrates the effect on the IASP of the PDE III/IV inhibitor zardaverine when injected i.p. (7.5 mg in vehicle) followed after 30 minutes by a continuous infusion of a sub-threshold dose of isoproterenol.

The PDE III/IV inhibitor, zardaverine (7.5 mg in 100 µl 1M2P) was injected i.p. followed in 30 minutes by a continuous infusion of isoproterenol in saline at 0.2 µg/hour. Zardaverine, again induced a rapid and transient decrease in IASP. The isoproterenol infusion further reduced the IASP to almost zero mmHg (see FIG. 39). These experiments (FIGS. 36–39) suggest a potentiation of subthreshold levels of isoproterenol by zardaverine.

Example 18

Figure 40:
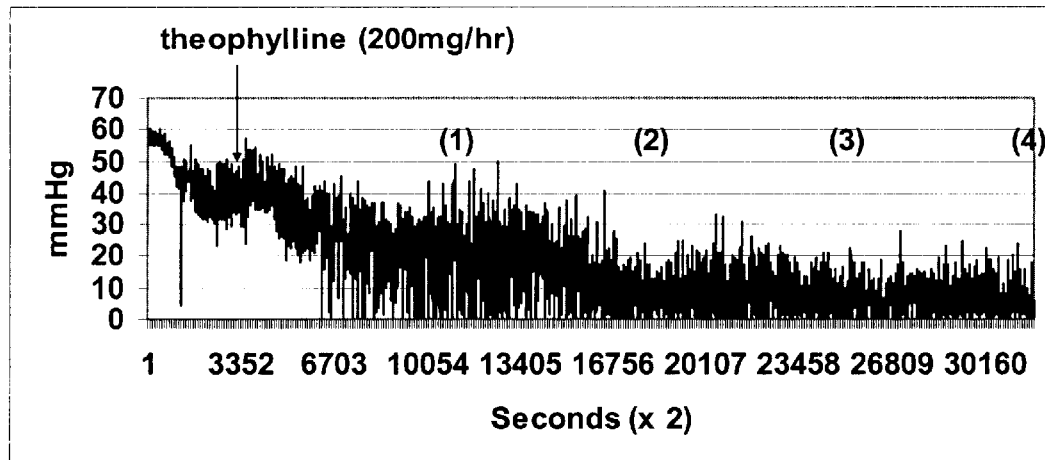
FIG. 40 illustrates the effect on the IASP of the adenosine antagonist and non-specific PDE inhibitor, theophylline when continuously infused at 200 μg/hour in 5% dextrose.

This example illustrates the use of adenosine antagonists to relax the IAS in the rat model.
Theophylline Theophylline, an adenosine antagonist, was continuously infused at 200 µg/hour in 5% dextrose. A dramatic and sustained drop in IASP was observed throughout the 4 hour duration of the experiment (see FIG. 40).

Figure 41:
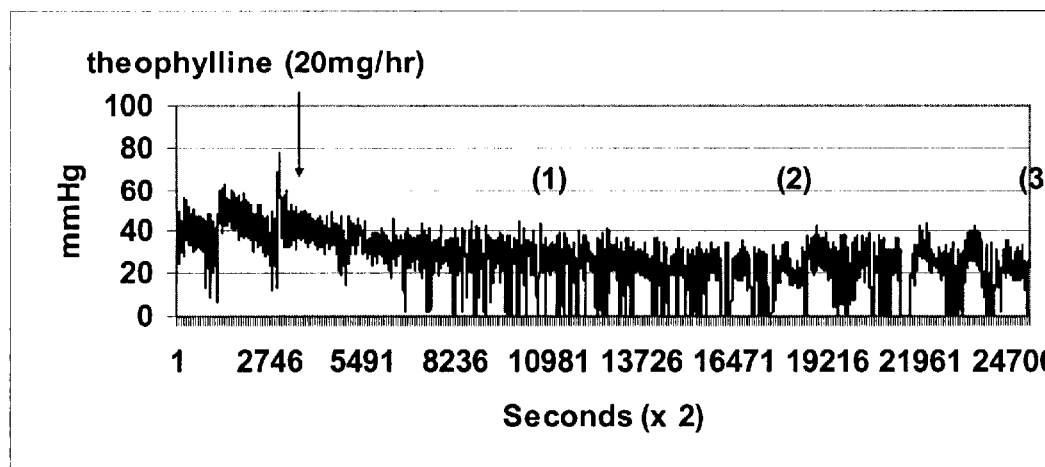
FIG. 41 illustrates the effect on the IASP of theophylline when continuously infused at 20 μg/hour in 5% dextrose.

Theophylline was continuously infused at 20 µg/hour in 5% dextrose. A moderate drop in average IASP was observed throughout the 3 hour duration of the experiment (see FIG. 41).

Figure 42:
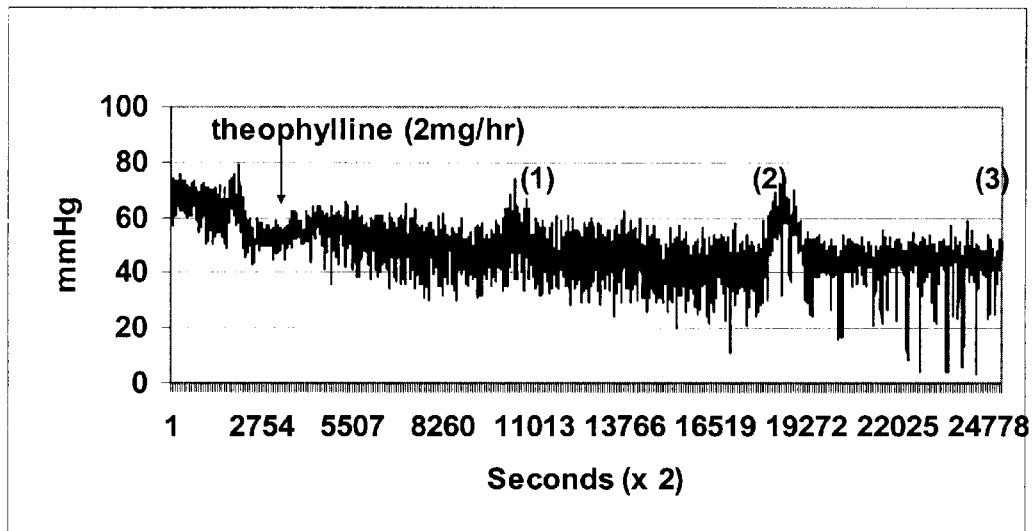
FIG. 42 illustrates the effect on the IASP of theophylline when continuously infused at 2 μg/hour in 5% dextrose.
Figure 43:
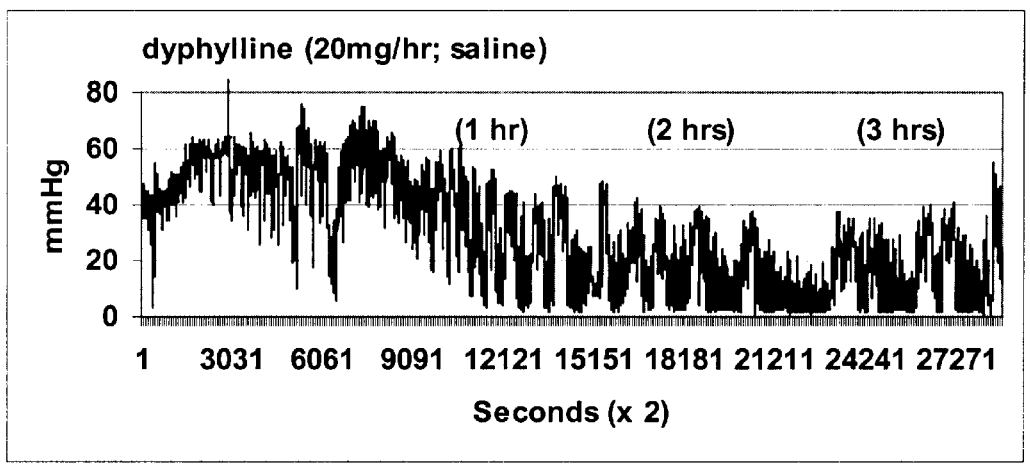
FIG. 43 illustrates the effect on the IASP of dyphylline when continuously infused at 20 μg/hour in 5% dextrose.

Theophylline was continuously infused at a lower dose, i.e. 2 µg/hour in 5% dextrose. A minimal drop in average IASP was observed throughout the 3 hour duration of the experiment (see FIG. 42).
Dyphylline FIG. 43 shows the IAS relaxing effects of a 20 µg/hr continuous dose of dyphylline [7-(2,3-dihydroxypropyl) theophylline], a theophylline derivative that is not metabolized by the liver and is excreted unchanged by the kidneys, providing this drug with a low toxicity potential.

Example 19

This example illustrates a method for treating anal disorders in an individual using phosphodiesterase inhibitors and other agents to reduce pain associated with the disorders, including acute and chronic anal fissures.

Patients with severe anal pain and especially during and after bowel movement can be treated with the following therapies: zaprinast, zaprinast and nitroglycerin, minoxidil, nitroglycerin and cGMP mimetics, isoproterenol, or sildenafil, either one to three times daily or as required to effectively reduce anal rectal pain. Pain reduction (indicated by a reduction in the average pain and/or the defecation pain) will be evaluated and the time to pain reduction will also be evaluated. Therapy that is effective in relieving anal pain will eventually leads to effective resolution of these anal rectal disorders. Additionally, drugs that can effectively reduce anal sphincter pressure, maintain reduced anal sphincter pressure, or prevent recurrence of the diseases and yet cause minimal or no adverse reactions such as headache, dizziness, and hypotension will be of great therapeutic benefit.

Example 20

This example illustrates a method for treating anal disorders in an individual using phosphodiesterase inhibitors and other agents to promote healing in acute and chronic anal fissures.

Patients with anal fissures can be treated with the following therapies: zaprinast, zaprinast and nitroglycerin, minoxidil, nitroglycerin and cGMP mimetics, isoproterenol, or sildenafil, either one to three times daily or as required to effectively promote healing. Healing is indicated by improving re-epithelization of the observed fissure and can be evaluated along with the time needed to complete healing. Therapy that is effective in healing anal fissures eventually leads to complete resolution of these anal rectal disorders. Furthermore, drugs that can effectively reduce anal sphincter pressure, maintain reduced anal sphincter pressure, or prevent recurrence of the diseases and yet cause minimal or no adverse reactions such as headache will provide significant medical benefit.

Example 21

This example illustrates a method to reduce bleeding in patients with hemorrhoidal symptoms or diseases.

Patients with hemorrhoidal symptoms or diseases can be treated with the following therapies: zaprinast, zaprinast and nitroglycerin, minoxidil, nitroglycerin and cGMP mimetics, isoproterenol, or sildenafil, either one to three times daily or as required to effectively reduce bleeding and promote healing. Disease resolution indicated by reduction in bleeding and or pain can be evaluated along with the time to healing. Therapy that is effective in improving hemorrhoidal symptoms will eventually lead to complete resolution of these anal rectal disorders. Furthermore, drugs that can effectively reduce anal sphincter pressure, maintain reduced anal sphincter pressure, or prevent recurrence of the diseases while causing minimal or no adverse reactions such as headache are of significant medical benefit.

Example 22

A composition of a base gel comprising 1.0 gm of salbutamol, 0.6 gm of carbopol 1342 USP, 35.44 gm of propylene glycol, 15.16 gm of dehydrated ethanol USP, 15.16 gm of isopropyl alcohol USP, 2.5 % oleic acid, triethanolamine HCl 1N to adjust the pH from 6.0 to 7.0, 0.05 gm of butylated hydroxytoluene NF, and 29.72 gm of purified water USP. Other concentrations of salbutamol can be added in the same gel base to achieve the therapeutically effective dose; this can also be achieved by adjusting the concentration of other β-agonists with gel base excipients such as oleic acid.

Example 23

One example of a topical composition comprises 0.05 to 1% sildenafil, 75% (w/w) white petrolatum USP, 4% (w/w) paraffin wax USP/NF, lanolin 14% (w/w), 2% sorbitan sesquioleate NF, and 4% propylene glycol USP at the therapeutic effective dose to the anorectal area. Typically, the 50 mg to 600 mg of sildenafil ointment can be applied to the anorectal area in order to reduce the signs and/or symptoms associated with anorectal disorders, for example, anal fissure, anal ulcers, and hemorrhoidal diseases. The concentration of sildenafil, or other phosphodiesterase inhibitors can be varied by adjusting the ratio between the sildenafil with excipients facilitate either the attachment of sildenafil to the local tissue, or agents enhance absorption to the afflicted tissue.

Yet another example of a topical composition comprises nitroglycerin at 0.1% concentration and sildenafil at 0.1% concentration can be incorporated in the same ointment base as mentioned above. This composition can be applied topically from a metered dosing device where a 50 mg to 1.5 gm dose of the composition is administered to the afflicted anorectal tissue to achieve the desired therapeutic effects.

Another therapeutic regimen is to provide patients afflicted with the anorectal disorders with both oral sildenafil tablets and topical nitroglycerin ointment. These two dosage forms can be used in combinations which provide the best efficacy and compliance among these patients.

Example 24

A composition of aminothylline topical spray composition comprises 0.1 to 5.0% (w/w) of aminothylline, acetylated lanolin alcohol, aloe vera, butane, cetyl acetate, hydrofluorocarbon, methyl paraben, PEG-8 laurate and polysorbate 80 in a 2 oz. pump spray bottle. The concentration of aminophylline or other non-specific phosphodiesterase inhibitor can vary between 0.5% to 5%. Other non-hydrofluorocarbon propellant can also be used instead of hydrofluorocarbon in the current composition. This composition can be sprayed directly onto the afflicted tissue once to four times daily to achieve the desired relief of signs and/or symptoms associated with anorectal disorders. This composition can also include menthol and benzocaine to provide the immediate local pain relief and soothing sensation whereas aminophylline provides the longer lasting relaxation of anal sphincter pressure.

Example 25

A base cream composition comprises 2 gm prazosin hydrochloride (2.0% w/w), 54.3 gm of purified water USP, 2 gm of Sepigel 305, 4.5 gm of Crodamol, 5.0 gm of glycerin, 6.0 gm sesame oil, 15.0 gm of white petrolatum USP, 2.0 gm of lanolin USP, 7.0 gm of 1,3-butylene glycol, 0.2 gm of methylparaben and 2.0 gm of silicon HL88.

A base cream can be prepared by first separate mixings of aqueous versus non-aqueous, i.e. oil phase, components of the cream. Once the aqueous phase containing the prazosin hydrochloride is well mixed, the melted oil phase is gently stirred into the aqueous phase to form a uniform cream base.

Example 26

Sildenafil, a specific inhibitor of type V phosphodiesterase, can be given orally via a tablet, parenterally or can be applied topically to patients diagnosed with anal fissures, either acute or chronic anal fissures, or other anorectal disorders. Sildenafil can be given one to three times daily for 8 weeks, especially in the case of patients afflicted with chronic anal fissure to cause the reduction of signs and symptoms associated with anorectal disorders.

For topical application, an approximate 50 mg to 900 mg dose of the cream measured by a metered dosing device, containing sildenafil, at the concentration from 0.02% to 5%, can be applied to the afflicted anorectal region using an applicator or by finger, one to four times daily to achieve the desirable therapeutic effects. Alternatively, the oral and topical treatment can be used in a defined regimen to achieve the best therapeutic effects.

Example 27

A phosphodiesterase inhibitor, for example aminophylline, can be given either orally via a tablet, parenterally or can be applied to patients diagnosed with anal fissures or other anorectal disorders, either acute or chronic anal fissures from a topical dosage form, e.g. a cream. For topical application, an approximate 50 mg to 900 mg of the cream measured by a metered dose device, can be applied to the afflicted anorectal region using an applicator or by finger, one to four times daily to achieve the desirable therapeutic effects.

Example 28

A β-adrenergic agonist, for example salbutamol, can be given from a suppository dosage form to patients diagnosed with anal fissures or other anorectal disorders, either acute or chronic anal fissures from a topical dosage form, e.g. a cream. For suppository application, an approximate 300 mg to 3 gm of the suppository unit can be applied to the afflicted anorectal region using an applicator or by finger, one to four times daily. Once the suppository melts in the anal cavity, the salbutamol released from the dosage form is available to achieve the desirable therapeutic effects.

Example 29

A α-adrenergic antagonist, i.e. prazosin can be applied from a topical spray to patients diagnosed with hemorrhoidal disorders, alone or in combination with a local anesthetic, for example, lidocaine, or in combination with a mixed $β_2$- and $β_3$-adrenergic agonist, for example salbutamol, or in combination with a PDE IV inhibitor, for example, ariflo (SB207499), RP73401, CDP840, rolipram and LAS31025. Prazosin can be applied directly to the afflicted area with the propellant from the spray and can be used as needed to relieve the local pain and anal sphincter hypertonicity. Eventually, the application of prazosin leads to healing of the hemorrhoidal disorders.

Example 30

This example illustrates the preparation of a theophylline topical formulation from theophylline oral tablets.

Five Theo-24 tablets (400 mg of theophylline per tablet; UCB Pharmaceuticals, Inc.) were combined and ground into a fine powder. To this powder, 50 ml of ethanol was added and the solution was stirred at room temperature for 15 minutes. Next, 48 ml of propylene glycol and 100 ml of distilled water were added to the ethanol mixture while stirring. This mixture was stirred for 15 minutes, at which time the powder was completely dissolved. A solution of carbopol in distilled water was then added to the mixture while stirring, forming a 1% topical theophylline gel. The resulting gel was then stirred for another 15 minutes.

Example 31

A methylxanthine derivative, for example diphylline or theophyllline, can be given either orally via a tablet, parenterally or can be applied to patients diagnosed with anal fissures or other anorectal disorders, either acute or chronic anal fissures from a topical dosage form, e.g. a cream or a rectal suppository.

For topical application, an approximate 50 mg to 900 mg of the cream measured by a metered dose device, can be applied to the afflicted anorectal region using an applicator or by finger, one to four times daily to achieve the desirable therapeutic effects.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of treating an anorectal disorder, and for controlling the pain associated therewith, the method comprising administering to a subject in need of such treatment a therapeutically effective amount of a composition that consists essentially of an adenosine receptor antagonist.

2. A method of treating an anorectal disorder, and for controlling die pain associated therewith, the method comprising administering to a subject in need of such treatment a therapeutically effective amount of a composition that consists essentially of an adenosine receptor antagonist and an internal anal sphincter relaxing agent wherein the said relaxing agent is NO donors.

3. The method of claim 2, wherein said NO donor is nitroglycerin, SNAP, GSNO or SIN-1.

4. The method of claim 2, wherein said NO donor is L-arginine.

5. A method of treating an anorectal disorder, and for controlling the pain associated therewith, the method comprising administering to a subject in need of such treatment a therapeutically effective amount of a composition that consists essentially of a methyl xanthine.

6. The method of claim 5, wherein said adenosine receptor antagonist is theophylline or dyphylline.

7. The method of claim 2, wherein the administering is local.

8. The method of claim 2, wherein said composition is formulated for topical application.

9. The method of claim 5, wherein the administering is local.

10. The method of claim 5, wherein said composition is formulated for topical application.

* * * * *